(12) United States Patent
McGuire

(10) Patent No.: US 6,547,793 B1
(45) Date of Patent: Apr. 15, 2003

(54) SYSTEMS AND METHODS FOR PRODUCING OSTEOTOMIES

(75) Inventor: David A. McGuire, 3418 Lakeside Dr., Anchorage, AK (US) 99515

(73) Assignee: David A. McGuire, Anchorage, AK (US)

( * ) Notice: Subject to any disclaimer, the term of this patent is extended or adjusted under 35 U.S.C. 154(b) by 0 days.

(21) Appl. No.: 09/506,714

(22) Filed: Feb. 18, 2000

Related U.S. Application Data

(62) Division of application No. 08/985,568, filed on Dec. 5, 1997, now Pat. No. 6,027,504.
(60) Provisional application No. 60/031,989, filed on Dec. 6, 1996, and provisional application No. 60/063,195, filed on Oct. 21, 1997.

(51) Int. Cl.[7] .............................................. A61B 17/86
(52) U.S. Cl. .......................................... 606/73; 606/87
(58) Field of Search .............................. 606/60, 62, 65, 606/66, 72, 73

(56) References Cited

U.S. PATENT DOCUMENTS

| | | | |
|---|---|---|---|
| 624,969 A | 5/1899 | Peterson | |
| 1,269,912 A | 6/1918 | Dunham | |
| 2,077,804 A | 4/1937 | Morrison | 128/83 |
| 2,485,531 A | * 10/1949 | Dzus et al. | |
| 2,511,051 A | 6/1950 | Dzus | 128/92 |
| 2,685,877 A | 8/1954 | Dobelle | 128/92 |
| 3,716,051 A | 2/1973 | Fischer | 128/92 BB |
| 4,398,855 A | 8/1983 | Hultquist | 411/340 |
| 4,409,973 A | 10/1983 | Neufeld | 128/92 E |
| 4,519,100 A | 5/1985 | Wills et al. | 128/92 C |
| 4,550,449 A | * 11/1985 | Tunc | |
| 4,632,101 A | 12/1986 | Freedland | 128/92 YW |
| 4,721,103 A | 1/1988 | Freedland | 128/92 YW |
| 4,776,329 A | * 10/1988 | Treharne | |
| 4,862,883 A | 9/1989 | Freedland | 128/92 YZ |
| 5,098,433 A | 3/1992 | Freedland | 606/63 |
| 5,226,767 A | * 7/1993 | Foerster, Jr. | |
| 5,413,579 A | 5/1995 | DuToit | 606/87 |
| 5,584,836 A | 12/1996 | Ballintyn et al. | 606/73 |
| 5,613,969 A | 3/1997 | Jenkins, Jr. | 606/87 |
| 5,722,978 A | 3/1998 | Jenkins, Jr. | 606/87 |
| 5,893,850 A | * 4/1999 | Cachia | |

FOREIGN PATENT DOCUMENTS

FR                2567016              1/1986

* cited by examiner

*Primary Examiner*—David O. Reip
(74) *Attorney, Agent, or Firm*—Bromberg & Sunstein LLP

(57) ABSTRACT

Systems and methods for producing minimally invasive osteotomies to correct angular deformities of bones in and about the knee are disclosed. A method includes locating a plane in which the angle exhibited by the deformity is situated. An oblique cut is then made along a surface of the bone, such that the cut is transverse to the plane in which the angle is situated. Thereafter, the bone pieces are rotated about the cut relative to one another until a desired alignment between the bone pieces is achieved. To maintain the bone pieces in alignment, a device having an elongated body for extending into a tunnel between the bone pieces is provided. The system also includes a rigid member fixedly positioned at one end of the body. The rigid member is transverse to the body to engage one bone piece. The system further includes a locking mechanism at an opposite end of the body to engage the other bone piece. The system permits the bone pieces to be pulled against one another between the rigid member and the locking mechanism.

13 Claims, 26 Drawing Sheets

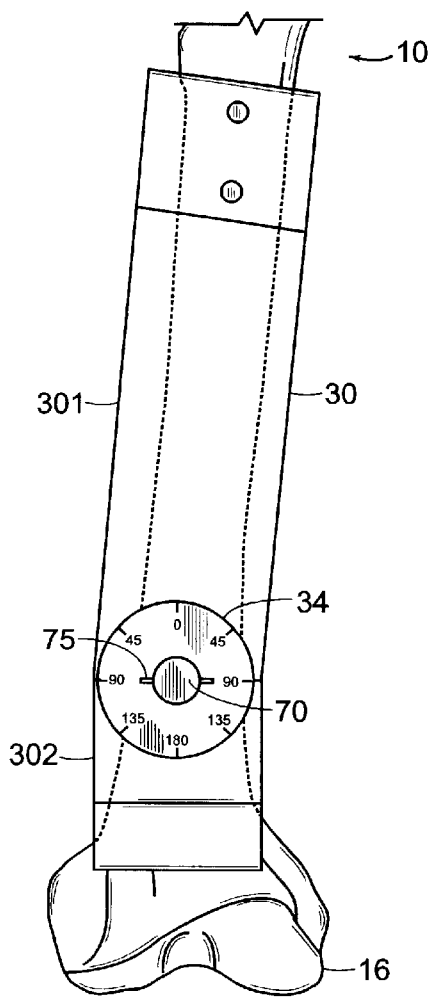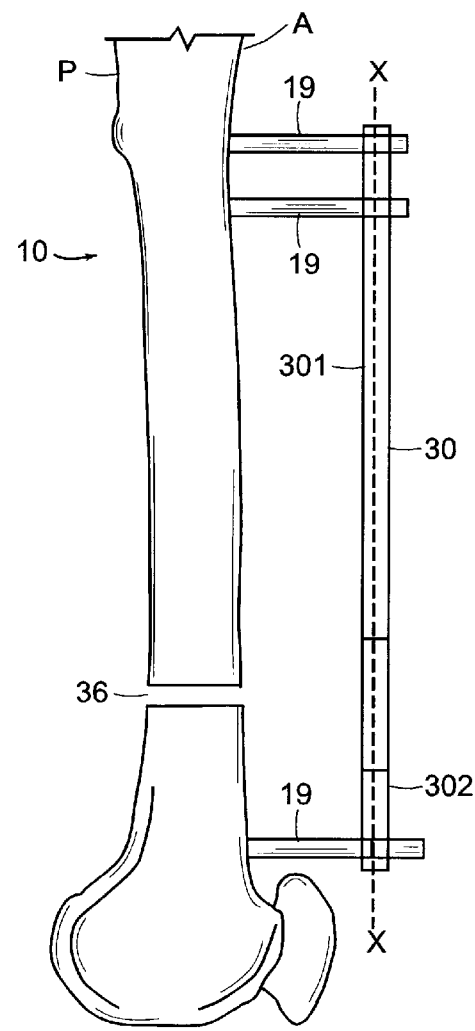
FIG. 3A                    FIG. 3B

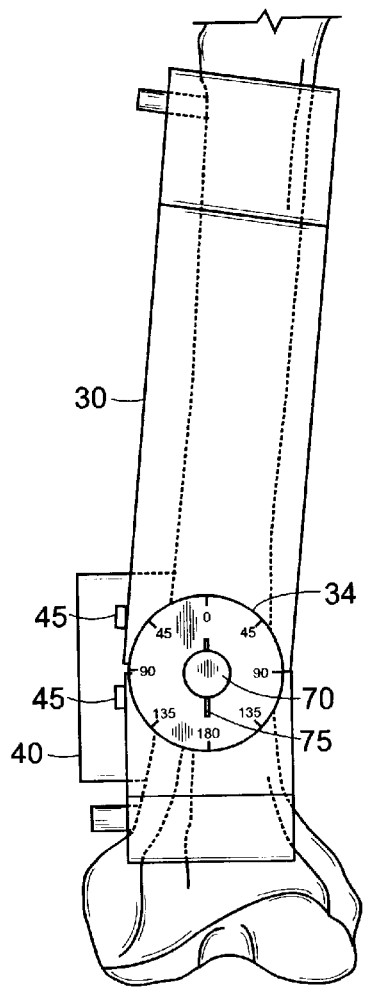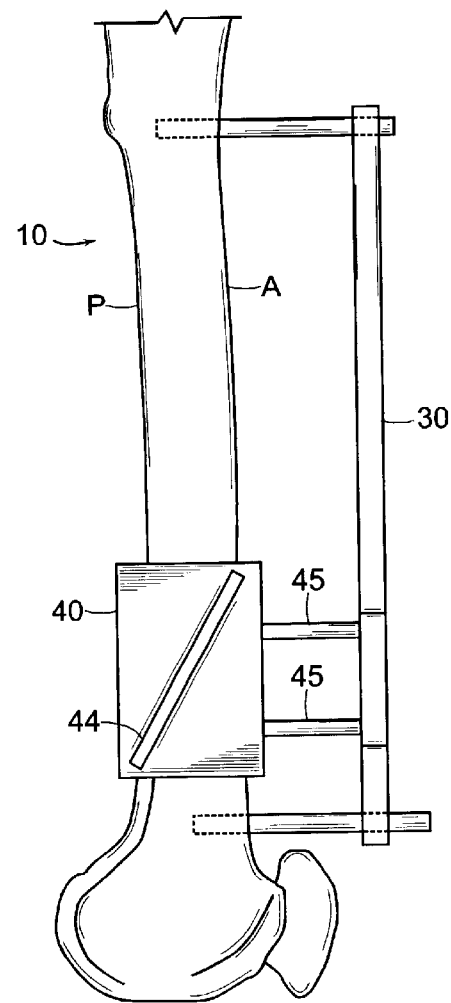
FIG. 4C
FIG. 4D

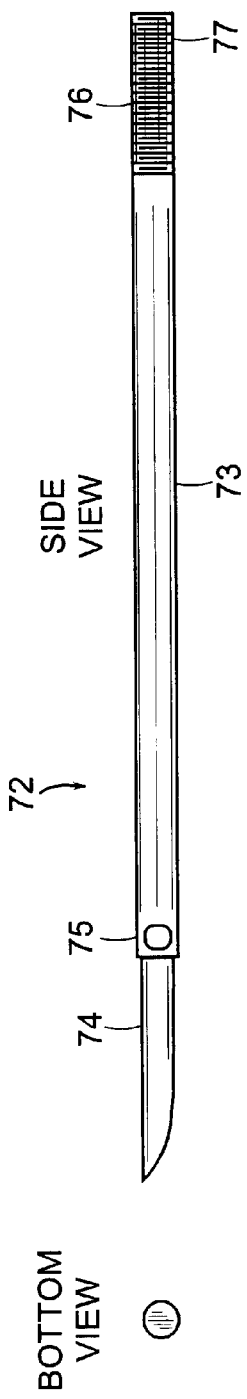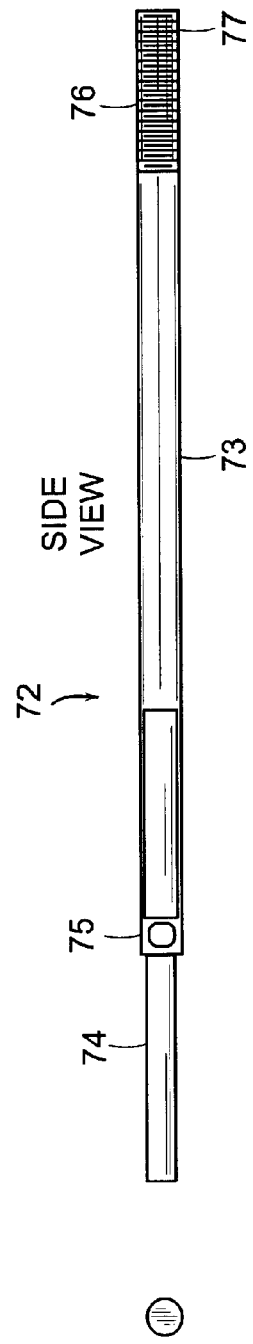
FIG. 8A
FIG. 8B

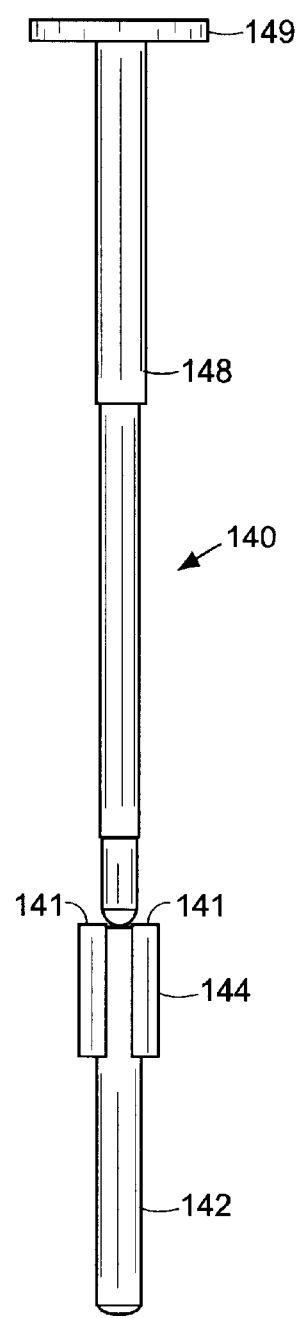
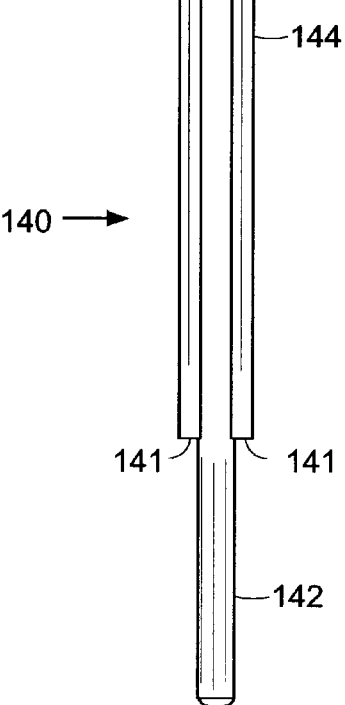
FIG. 14C
FIG. 14D

SYSTEMS AND METHODS FOR PRODUCING OSTEOTOMIES

RELATED U.S. APPLICATION(S)

The present application claims priority from U.S. Provisional Application No. 60/031,989, filed Dec. 6, 1996 and from U.S. Provisional Application No. 60/063,195, filed Oct. 21, 1997, and is a copendent, divisional application of U.S. Utility application Ser. No. 08/985,568 filed Dec. 5, 1997, now U.S. Pat. No. 6,027,504, which are all hereby incorporated herein by reference.

TECHNICAL FIELD

This invention relates to a device and method for producing osteotomies in bones experiencing angular deformities, and in particular osteotomies associated with angular deformities of the femur and tibia.

BACKGROUND ART

Prior art methods for producing osteotomies to correct angular deformity in a bone mass, such as a femur or tibia, generally require making a large open incision around the deformed site and cutting a wedge, at such site, completely across the deformed bone mass, to initially form two bone pieces. Once the cut has been made in the bone mass and the wedge removed, the bone pieces may be realigned and the angle between the two bone pieces adjusted for corrective purposes. However, because of the invasiveness of the surgery, osteotomy procedures often result in undesirable pain and extended period of immobility for the patient.

In addition to a period of immobility, prior art methods for producing osteotomies have allowed only minimal control of the bone pieces once the bone mass has been divided. For example, as it may be difficult to control the alignment between the two bone pieces of the deformed bone, the correction of the angular deformity may provide clinical results that are unpredictable. Also contributing to the unpredictability of the clinical results is the difficulty in maintaining the bone pieces in approximation after they have been aligned. Moreover, current osteotomy procedures typically involve application of a uniform corrective angle to the bone pieces, regardless of the individual. As individuals vary in height, weight and age, a slight difference in the angle of a deformed bone mass can cause a measurable difference in contact pressure between the articular surfaces of a deformed bone mass and another bone mass (e.g., between a deformed tibia and a femur). A uniform change in the angle of the deformed bone mass for different individuals, therefore, may not result in a sufficient change in the contact pressure between the articular surfaces of the bones, so as to avoid future degenerative problems.

Accordingly, there is a need for a method that produces osteotomies in a minimally invasive, predictable, and measurable manner, in addition to being individualized and reliable, so that the procedure may be performed at an early stage in the course of the disease. Such a method would permit avoidance of severe degenerative changes that frequently accompany current methods for producing osteotomies.

SUMMARY OF THE INVENTION

The present invention is directed to systems and methods for producing minimally invasive osteotomies to correct angular deformities of bones in and about the knee. The method of the present invention is accurate, reliable, predictable, measurable, controllable and reproducible. As hereinafter provided, the method is discussed in association with femoral and/or tibial osteotomies. However, it should be appreciated that the method has applications for other bones beyond those bones about the knee.

In accordance with one embodiment of the present invention, the method for producing osteotomy in a first bone having an angle of deformity includes drilling a tunnel through a surface of a first bone at an area about the angular deformity, such that the tunnel drilled is transverse to a plane in which the angle is situated. Next, an oblique cut is made partially across the bone on a surface that is parallel to the tunnel, so as to provide a cut that is at an angle to the tunnel. In an embodiment of the invention, the angle of the cut is such that when the bone is realigned, the contact pressure between an articular surface of the first bone and an articular surface of a second bone approaches a desirable ratio within a physiologic tolerance. Once the cut is partially made across the first bone, the first bone is secured about the cut, for instance, by placing through the tunnel a device which permits bone pieces of the first bone, once the first bone is completely cut, to be maintained in approximation. The amount of angular correction is then determined so that the contact pressure between the first and second bone may be brought to within physiological tolerance. In accordance with an embodiment of the invention, the angular correction is determined by measuring intra-articular pressure between the contact surfaces of the first and second bones. After the amount of angular correction has been determined, the cut is completed across the first bone to form two bone pieces. The bone pieces are then rotated relative to one another about the tunnel, so as to be brought into an alignment which brings about the desirable contact pressure between the first and second bones. The bone pieces are subsequently secured against one another to maintain alignment and close approximation.

In an embodiment of the present invention, the bone pieces are maintained in approximation by the use of a bone anchor assembly having an elongated body for extending across a juncture between the bone pieces. The elongated body includes a distal end and a proximal end. A rigid member is fixedly positioned at the distal end transverse to the body for engaging one bone piece. A locking mechanism is also provided at the proximal end of the body for engaging the other bone piece. To this end, the bone pieces may be pulled against one another between the rigid member at the distal end and the locking mechanism at the proximal end of the device.

Prior to drilling the tunnel through the deformed bone, a support structure of the present invention is preferably affixed along a surface of the deformed bone adjacent the angular deformity. The support structure is designed so that one end attaches to a first end portion of the bone, and an opposite end attaches to a second end portion of the bone. The support structure is also pivotally movable at an area between its ends. In this manner, once the bone pieces are formed, the support structure may maintain the bone pieces close to one another, so that they may subsequently be pivoted into alignment. To secure and maintain the bone pieces in approximation after alignment, a bone anchor assembly of the present invention is positioned through the tunnel and tightened against the bone pieces.

BRIEF DESCRIPTION OF THE DRAWINGS

FIGS. 3A–D correspond to FIGS. 1A–D respectively and further showing a support structure positioned along the anterior surface of the femur.

FIGS. 4A–D correspond to FIGS. 3A–D respectively and further showing a saw guide attached to the lateral surface of the femur.

FIGS. 8A–D show a bone anchor in accordance with one embodiment of the present invention.

FIG. 14A shows a longitudinal view, as well as a series of cross-sectional views illustrating progressively smaller inner diameters, in accordance with an embodiment. FIG. 14B is a cross-sectional view of another guide embodiment illustrating parallel contiguous inner passageways.

FIGS. 14C–D illustrate other embodiments of a guide for forming a bone anchor tunnel.

DETAILED DESCRIPTION OF SPECIFIC EMBODIMENTS

A preferred embodiment of the invention herein provides a device and method for producing minimally invasive osteotomies in and about the knee. In accordance with this embodiment, an osteotomy permits accurate, precise and controllable correction of angular deformities in bones about the knee, such that the amount of trauma typically associated with osteotomy is lessened. In order to provide an overall understanding of the present invention, the embodiments of the method of the invention will be discussed with reference to the embodiments of the devices of the invention. However, it will be understood by persons of ordinary skill in the art that embodiments of the invention are applicable to the production of osteotomies of other bones within the body.

There are two common types of angular deformities usually associated with the femur and tibia, valgus deformity and varus deformity. In either of these conditions, the angular deformity causes a deviation in the amount of contact pressure produced within the intra-articular space between the femur and the tibia, leading to degeneration of the knee joint. In general, valgus deformity, otherwise known as knock-kneed deformity, can be corrected by performing a femoral osteotomy to reduce the relatively high contact pressure between the lateral femoral condyle and the lateral tibial plateau, and increasing the relatively low contact pressure between the femoral medial condyle and the medial tibial plateau. Varus deformity, otherwise known as bow-legged deformity, on the other hand, can be corrected by performing a tibial osteotomy to reduce the relatively high contact pressure between the medial tibial plateau and the medial femoral condyle, and increasing the relatively low contact pressure between the lateral tibial plateau and the lateral femoral condyle.

Figure 1A:
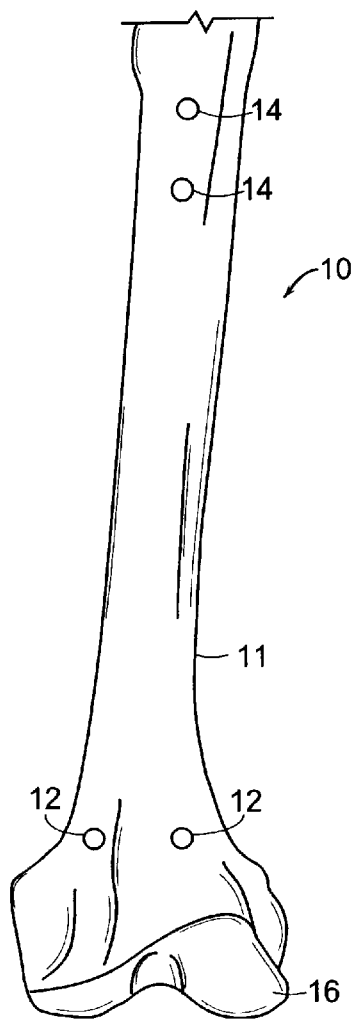
FIGS. 1A–D illustrate an angularly deformed femur having a plurality of holes formed in accordance with embodiments of the present invention, and having subcutaneously insertable pins situated within the holes.
Figure 1B:
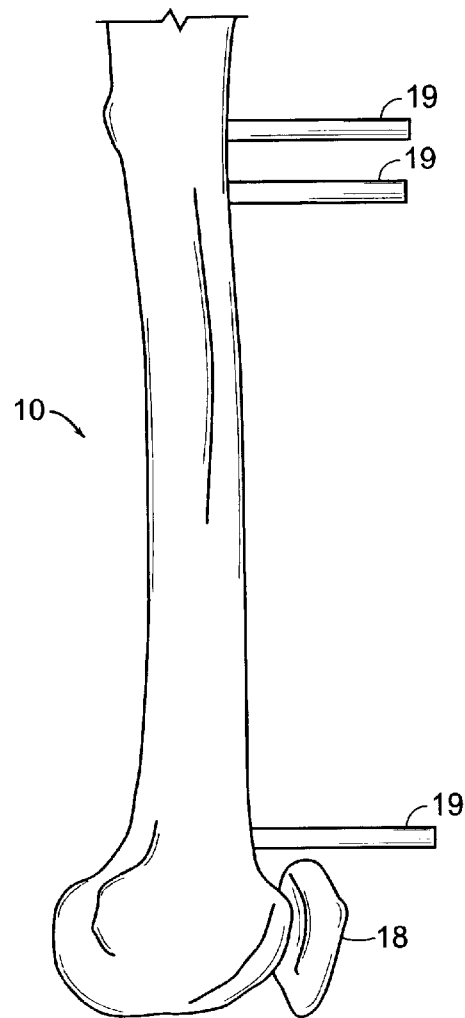
Figures 1C, 1D:
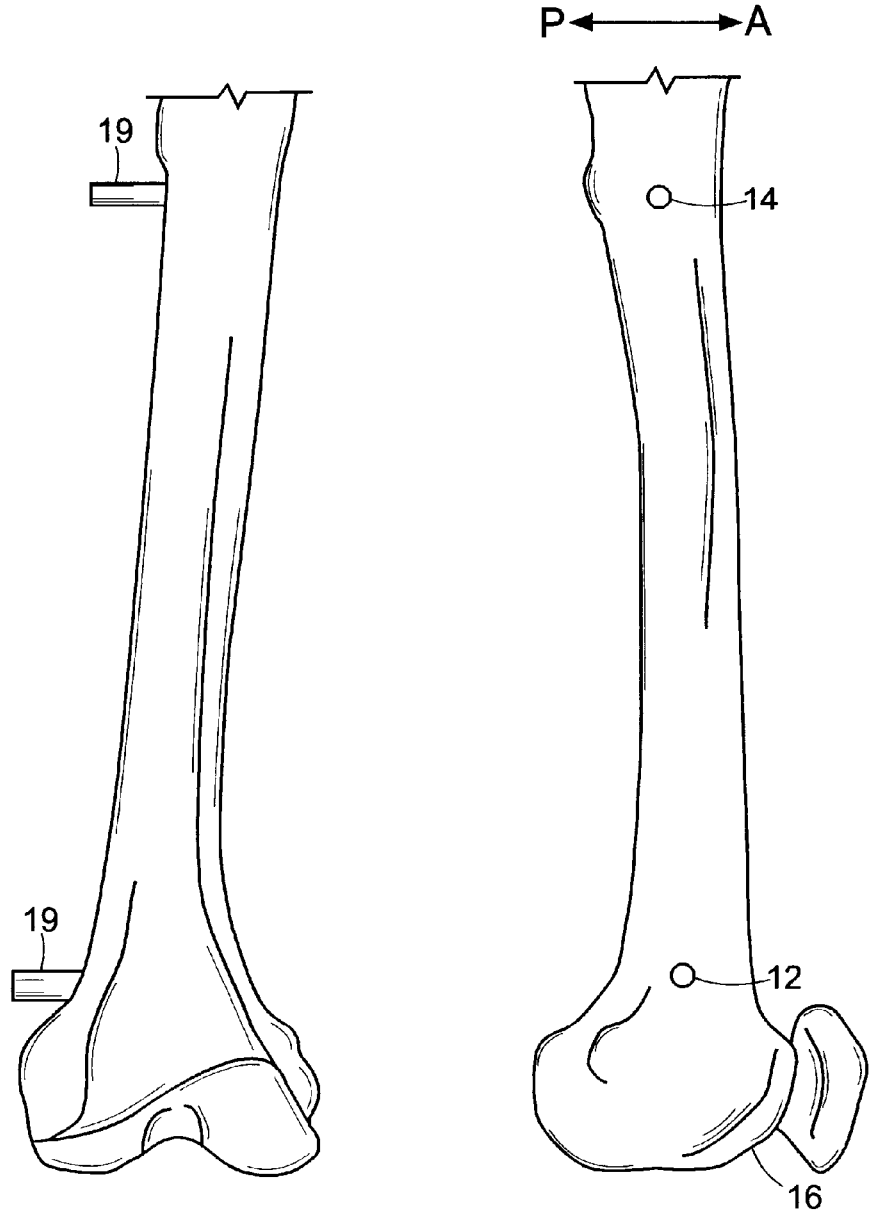

With reference now to femoral osteotomy, FIGS. 1A–D illustrate a femur 10 having an angular deformity 11 near its patellar surface 16. In FIG. 1A, sets of holes 12 and 14 are shown formed on the anterior surface of the femur 10 relative to the angular deformity 11. Holes 12 are formed near an end adjacent the patellar surface 16 and substantially parallel to the medial and lateral border of the patella 18. Holes 14, on the other hand, are formed toward an opposite end of the femur 10 relative to the deformity 11 and away from holes 12. Holes 12 and 14 establish sites at which subcutaneously insertable pins 19 may be placed for subsequent attachment of a femur support structure necessary for producing an osteotomy in accordance with an embodiment of the present invention. In a preferred embodiment, FIG. 1C shows one hole 12 and one hole 14 formed on the lateral surface of the femur 10. Hole 12 is formed toward the patellar surface 16 and is positioned substantially in the middle of femoral anterior-posterior diameter A-P. Hole 14, on the other hand, is positioned distal to hole 12 and sufficiently clear of an osteotomy site to be formed, so as not to interfere therewith. The use of a single hole, rather than a set of holes, may be desirable as there is less stripping and thus less damage to the soft tissue surrounding the femur 10.

Figure 2A:
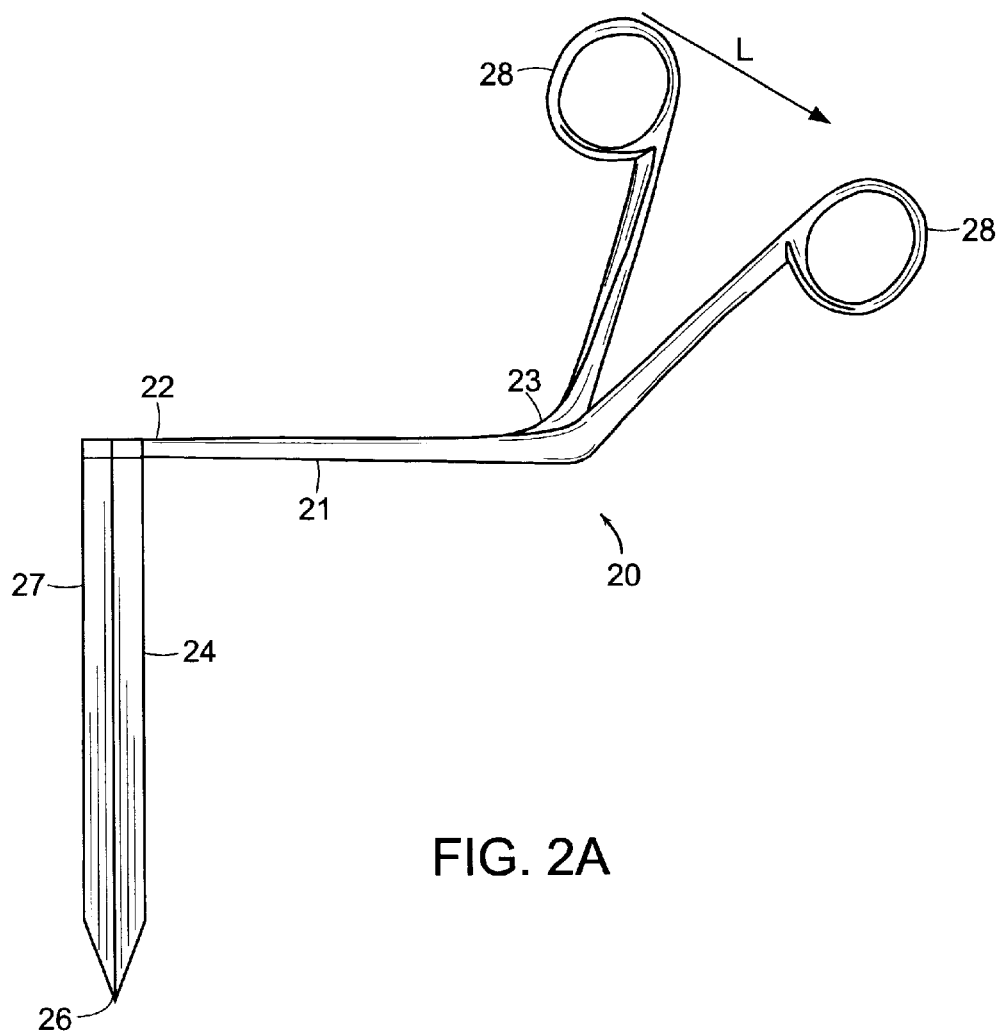
FIGS. 2A–D illustrate a separating device for use in the formation of the holes illustrated in FIGS. 1A–D.
Figure 2B:
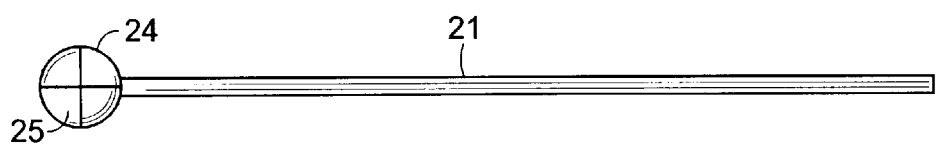
Figures 2C, 2D:
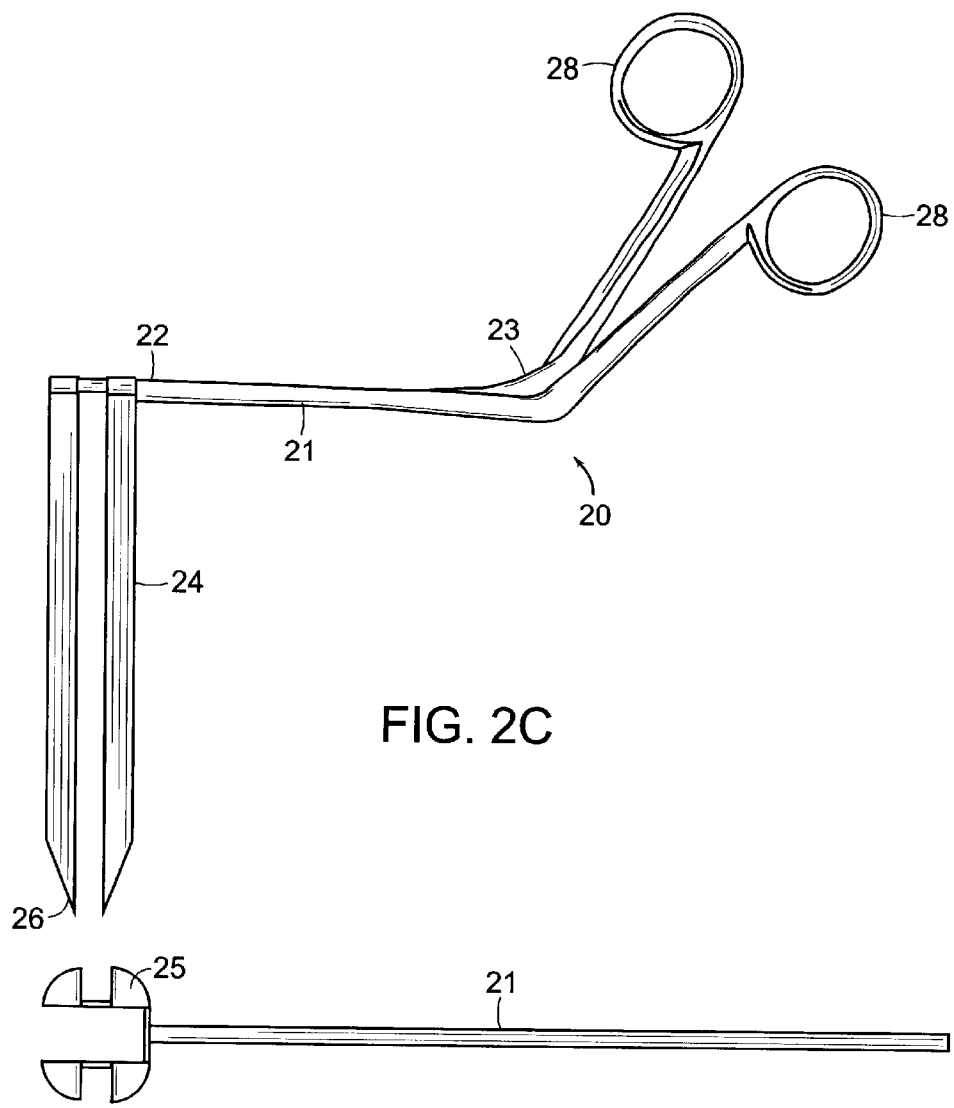

Referring now to FIGS. 2A–D, a device 20 is shown for exposing the underlying femur 10 of FIGS. 1A–D from the periosteum (i.e., soft tissue) that overlies the femur prior to producing holes 12 and 14. In accordance with an embodiment of the present invention, the device 20 includes an elongated body 21 having a first end 22 and a second end 23. The device also includes a spreading mechanism 24 located at the first end 22 of the body 21. The spreading mechanism 24, from the bottom view in FIG. 2B, is substantially cylindrical in cross-section, and includes four similarly shaped members 25. Each of the members 25 terminates in a sharp end 26, so as to allow the mechanism 24 to penetrate the soft tissue without the need for an incision or dissection of the soft tissue. A sheath 27, disposed about the spreading mechanism 24, is preferably bivalved so that it may conform to the spreading movement of the mechanism 24. The separating device 20 further includes actuating handles 28 located at the second end 23 of the body 21. After the mechanism 24 has penetrated the soft tissue, the handles 28, as shown in FIG. 2C, may be moved in the direction L of the arrow toward one another to spread the members 25 apart. Spreading the members 25, in the manner shown in FIG. 2D, causes spreading of the overlying soft tissue so as to expose the underlying femur 10. If necessary, a trocar (not shown) may be introduced into the newly created spread area so that subsequently a larger bivalve sheath may be inserted therein. The larger bivalve sheath in turn will allow progressive dilation of the soft tissue without the need for an incision into the soft tissue. Once the underlying femur 10 is exposed, a conventional surgical drill can be used to produce holes 12 and 14.

Referring again to FIGS. 1A–D, while FIG. 1A illustrates a set of two holes 12 and a set of two holes 14, a single hole can be provided in lieu of the set of holes 12 substantially between and slightly below the holes 12 in FIG. 1A. Alternatively, or in addition, a single hole may be utilized in lieu of the set of holes 14, positioned in the vicinity of such holes. Subcutaneously insertable pins 19 may be inserted into holes 12 and 14, as shown in FIGS. 1B and 1D. Pins 19 may be threaded so that they can be securely positioned within holes 12 and 14. Likewise, holes 12 and 14 may be complementarity threaded to receive threaded pins 19.

With the subcutaneously insertable pins 19 in place, looking now at FIGS. 3A–D, a support structure 30 may be affixed to the femur 10 via each of the pins 19. The support structure 30 is affixed in such a manner so that subsequent to the formation of two bone pieces during the osteotomy (discussed below), the bone pieces may be maintained in a desired alignment in close proximity to one another. Otherwise, it may be difficult to correct the angular deformity and to secure the bone pieces to one another. The support structure 30 includes a first portion 301 positioned away from the patellar surface 16 and a second portion 302 positioned adjacent the patellar surface 16. The first portion 301 and second portion 302 are mounted so as to pivot in the plane X—X in FIGS. 3B and 3D, but to preclude any substantial movement outside of the plane X—X.

Figure 3C:
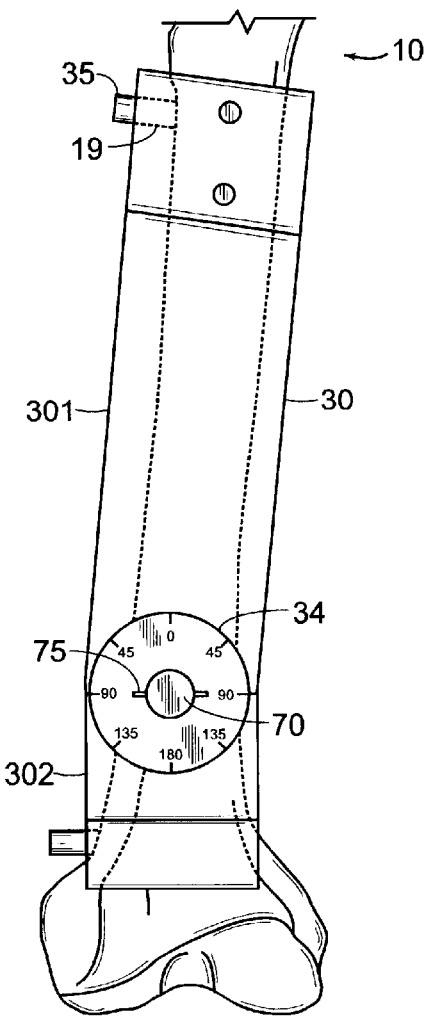
Figure 3D:
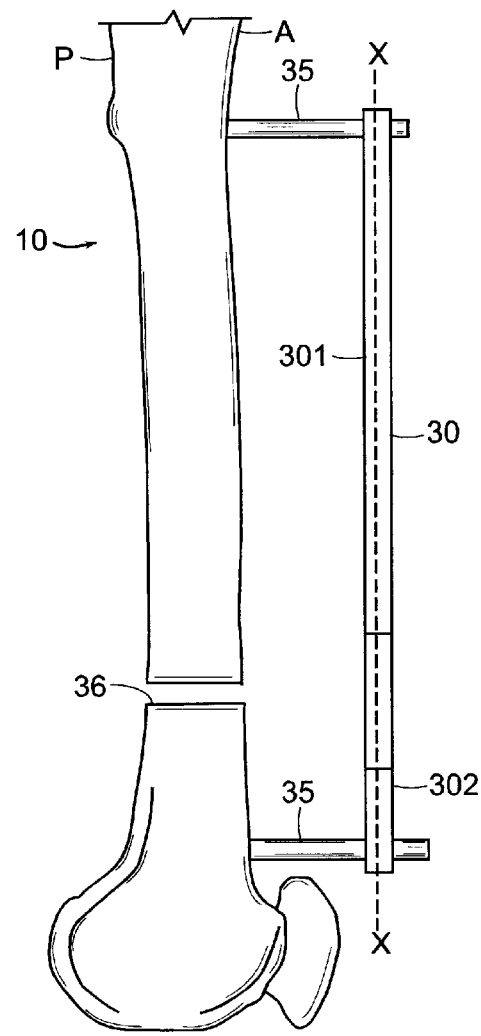

With particular reference now to FIGS. 3C–D, when the pins are situated on the lateral surface of the femur 10, the support structure 30, in accordance with a preferred embodiment of the invention, includes bars 35. Bars 35 are designed to extend at a substantially right angle from the upper and lower portions of the support structure 30 along the lateral surface of the femur 10, so that the bars 35 may be coupled to the pins 19. The support structure 30 shown in FIGS. 3C–D may also include a releasable locking mechanism (not shown) at the intersection between the bars 35 and the first and second portions 301 and 302 to provide rigidity to the support structure 30. If additional rigidity is desired, pins 19 may also be placed on the medial surface of the femur 10 opposite the pins 19 on the lateral surface, and the support structure 30 provided with additional bars 35 along the medial side for attachment to those pins 19.

To accurately control the alignment of bone pieces during the osteotomy, a goniometer 34 is positioned between the first portion 301 and the second portion 302 of support structure 30 to provide an accurate read out of the relative angle between the upper and lower portions. The preferred goniometer 34 is configured in such a manner that precise corrections to tenths of a degree or less may be achieved.

Once the support structure 30 has been affixed to the femur 10, the osteotomy may be performed in a number of ways. In one embodiment, a central tunnel 36, as shown in FIGS. 3B and 3D, is first drilled through the femur 10 near an approximate vertex of the angle exhibited by the deformity 11 and in a direction that is transverse to the plane in which such angle is situated. The tunnel 36 may be formed through opening 70 in the goniometer 40 by using a cannulated coring reamer (not shown) similar to that disclosed in U.S. patent application Ser. No. 08/475,015, entitled "Coring Reamer", filed Jun. 7, 1995, now U.S. Pat. No. 5,865,834, issued Feb. 2, 1999, in the name of the present inventor, and which is hereby incorporated herein by reference. When using the cannulated coring reamer, a guidewire may be placed in the femur 10 to facilitate the drilling of the tunnel 36. Additionally, the goniometer 34 may be placed at a sufficient distance from the femur 10 so that when the coring reamer moves through opening 70 and into the femur 10, the goniometer 34 may act as a guide to allow a substantially straight tunnel 36 to be drilled. A conventional drill (not shown) with a drill bit may also be used to form tunnel 36 through opening 70 in a similar manner. To guard against damage to the soft tissue surrounding the posterior surface of the femur, the coring reamer and the drill may be equipped with a stop (not shown) to limit the distance beyond which they can extend from the posterior surface of the femur. The tunnel 36 created in this embodiment is preferably substantially cylindrical in shape, and is intended for use with a suitable bone anchor (discussed below), such as shown in FIGS. 8A–8E, FIGS. 15A–B and FIGS. 16A–C.

Figure 14A:
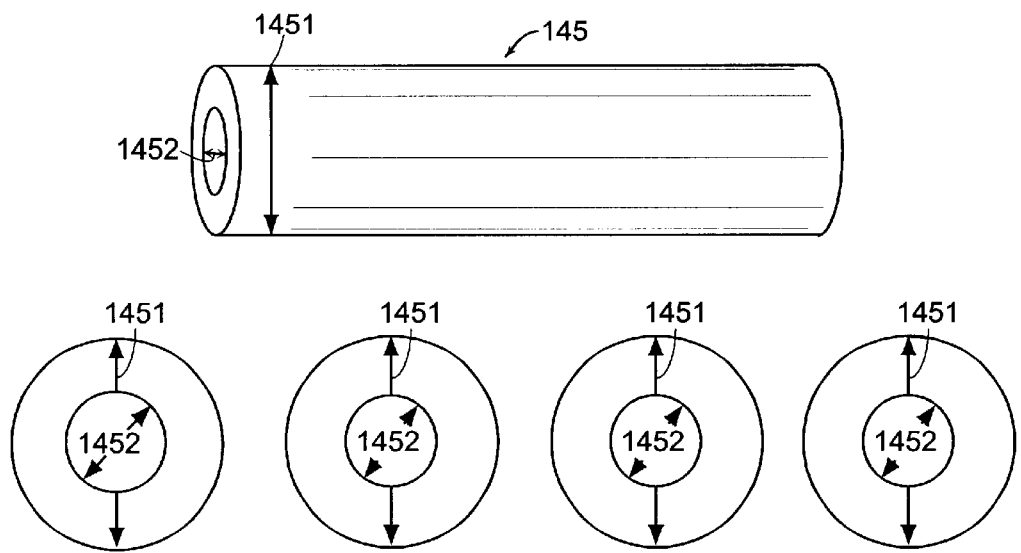
FIGS. 14A–B show alternate embodiments of a guide for forming a bone anchor tunnel.

Referring now to FIGS. 14A–D, to facilitate drilling of a substantially cylindrical tunnel 36, a rigid cylindrical guide 145, shown in FIG. 14A may be provided. Guide 145, in one embodiment, is provided with an outer diameter 1451 that is substantially similar to that of opening 70 in goniometer 34, and an inner diameter 1452 that is substantially similar to the diameter of the coring reamer or drill bit. If there arises a need to increase or decrease the diameter of the tunnel 36, a set of cylindrical guides 145 may be provided, whereby each guide would have the same outer diameter 1451, but a different inner diameter 1452 to match the diameter of the tunnel 36 to be created.

Figures 13A, 13B:
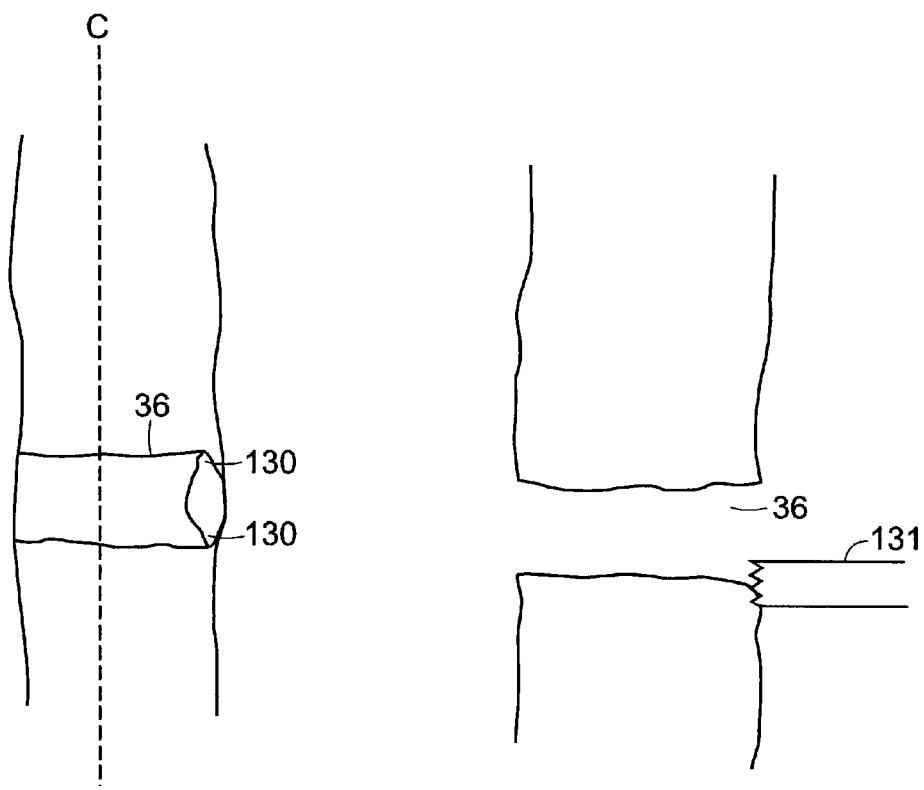
FIG. 13A shows an embodiment of a tunnel for use with a bone anchor in accordance with one embodiment of the present invention.
FIG. 13B illustrates a method for forming a tunnel in FIG. 13A through a femur.
Figure 13C:
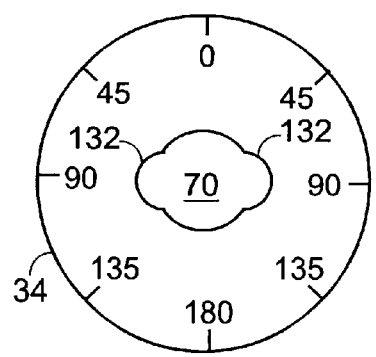
FIG. 13C shows a modified goniometer for forming tunnel shown in FIG. 13A.

In a related embodiment of the present invention, tunnel 36 may be modified, as shown in FIGS. 13A–B to include a pair of parallel contiguous passageways 130 on opposite sides of the tunnel to accommodate another style of bone anchor described below, such as illustrated in FIGS. 15A–15B and 16A–16C. To form passageways 130, a second reamer 131 having a diameter substantially smaller than the diameter of the cannulated coring reamer is used. The second reamer 131, like the coring reamer, may be cannulated for use with a guidewire. A first passageway 130 may be formed by placing the second reamer against an edge on one side of tunnel 36 (FIG. 13B) and pushing the second reamer through the femur 10 along the entire length of the tunnel. In order to place the second reamer against an edge of the tunnel 36, it should be appreciated that opening 70 in goniometer 34 may need to be modified so that its profile matches that of tunnel 36 shown in FIG. 13A. The opening 70, therefore, may be provided with widened areas 132, shown in FIG. 13C, to accommodate the second reamer when it is introduced along the sides of tunnel 36. After one passageway is formed, a second passageway 130 may then be formed along an opposite side of the tunnel 36 by placing the second reamer through the other widened area 132. The passageways 130 are formed so that each intersects or overlaps with an edge of the tunnel 36.

Figure 4A:
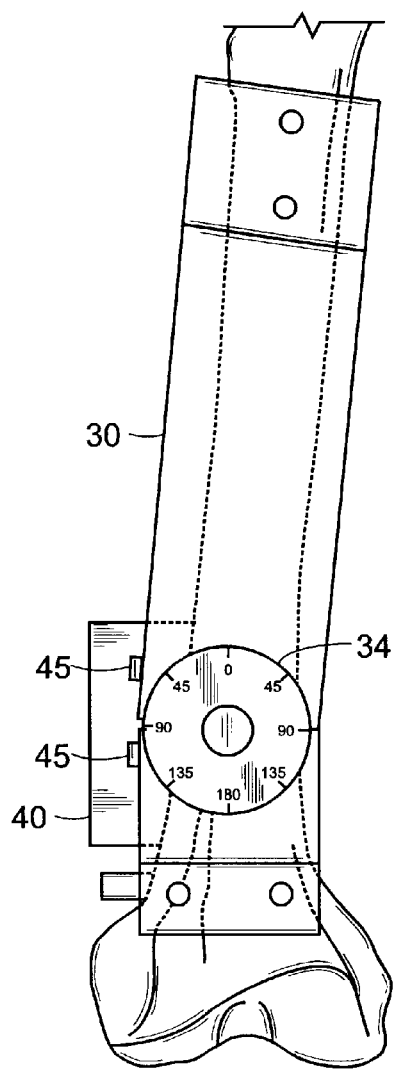
Figure 14B:
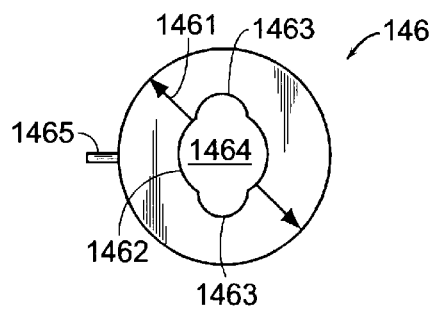

The passageways 130 along opposite sides of tunnel 36 may also be formed by using a reamer or drill bit in combination with a rigid cylindrical guide 146, illustrated in FIG. 14B. Cylindrical guide 146, in accordance with a preferred embodiment of the invention, includes an outer diameter 1461 that is substantially similar to that of the opening 70 in the goniometer 34, and an inner profile 1462 that includes widened areas 1463 on opposite sides of a central opening 1464. To form passageways 130 using guide 146, a cylindrical guide 145 with an inner diameter 1452 sufficiently sized to accommodate a bone anchor may initially be used to form a cylindrical tunnel 36. Thereafter, the cylindrical guide 145 is removed from the opening 70 and replaced with the guide 146. Guide 146 preferably includes a profile wherein the central opening 1464 is similar in diameter to the cylindrical tunnel 36 just created, and wherein the widened areas 1463 extend radially from the central opening. By way of example, if the goniometer 34 is provided with an opening 70 having a diameter of about 10 millimeters to about 12 millimeters (mm), the cylindrical guide 145 preferably includes an inner diameter 1452 for forming a tunnel that is about 6 mm to about 8 mm in diameter, and the guide 146 should have an inner profile 1462 with a central opening 1464 that is about 6mm and widened areas 1463 that extend radially about 1 mm to about 2 mm on each side of the central opening 1464. Once the guide 146 is in place, passageways 130 may be formed by drilling through the widened areas 1463. In an embodiment of the invention, the passageways 130 are formed so that they aligned longitudinally along a central axis C of the femur 10, such as that shown in FIGS. 13A and 15B. To ensure that the passageways 130 are directly opposite one another, guide 146 must be prevented from rotating from its original position after the formation of one passageway 130. To this end, the guide 146 may be configured to include at least one protrusion 1465 on its outer diameter 1461, and the goniometer 34 may be configured to include at least one slot 75, as shown in FIGS. 3A and 3D, abutting the opening 70 to receive the protrusion 1465. Of course, the passageways 130 may be formed so that they are through to the axis C. The slot 75, in this embodiment, would then be moved to a position shown in FIG. 4C to accommodate the protrusion 1465.

Substantially straight passageways 130 may also be formed along opposite sides of tunnel 36 by employing a guide 140, shown in FIGS. 14C and 14D. The guide 140 includes a distal portion 142 to be inserted into tunnel 36. The distal portion 142 preferably has a width substantially similar to the diameter of tunnel 36. In this manner, guide 140 can snugly fit within tunnel 36. The guide 140 further includes an optional sleeve 144 axially attached to the distal portion 142. The optional sleeve 144 is provided with at least two (2) opposing channels 141, so as to guide a reamer or drill bit alongside the tunnel 36. If desired, additional opposing channels may be provided circumferentially about the sleeve 144, so as to decrease the amount of rotational alignment needed for drilling the passageways. Extending posteriorly from the sleeve 144 is an elongated proximal portion 148, which terminates in a stop 149. The stop 149 may include holes 147 corresponding in number and in alignment with channels 141. The proximal portion 148 and stop 149 provide a surgeon with a place to hold and maneuver the guide 140 into the tunnel 36. If desired, the elongated proximal portion 148 may be removably attachable to the sleeve 144. Alternatively, the elongated proximal portion 148 may be made integral with sleeve 144. Once the guide 140 is in place, a reamer or drill bit may be introduced through a hole 147 in the stop 149, through a channel 146 in sleeve 144, and along the proximal portion 148 to drill a substantially straight passageway 130. The optional sleeve 144 with channels 146 facilitate alignment of the drill parallel with that of bone tunnel 36. Guide 140 may also include a protrusion, similar to protrusion 1465 in guide 146, for mating with a slot 75 in the goniometer 34 to insure that the passageways 130 are substantially opposite to one another when being drilled.

Figure 4B:
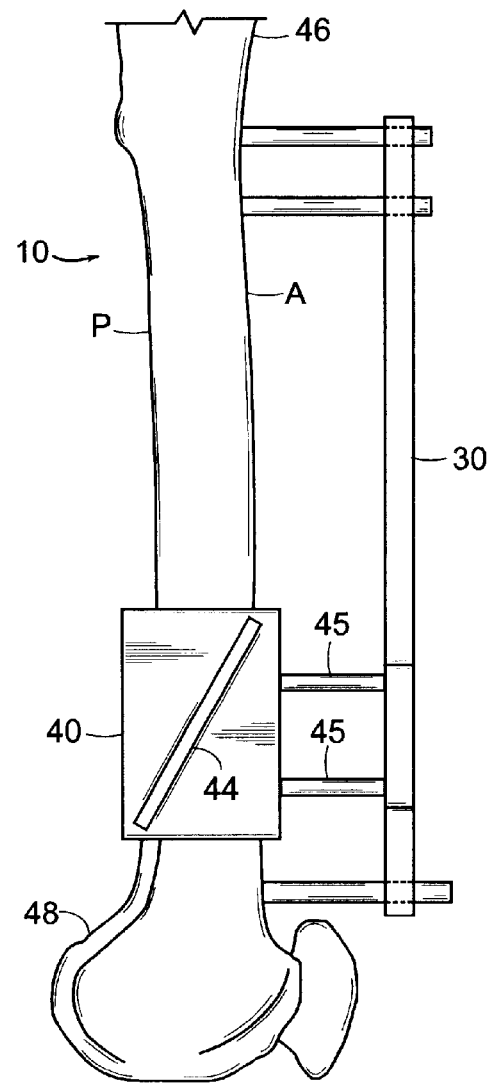
Figure 5:
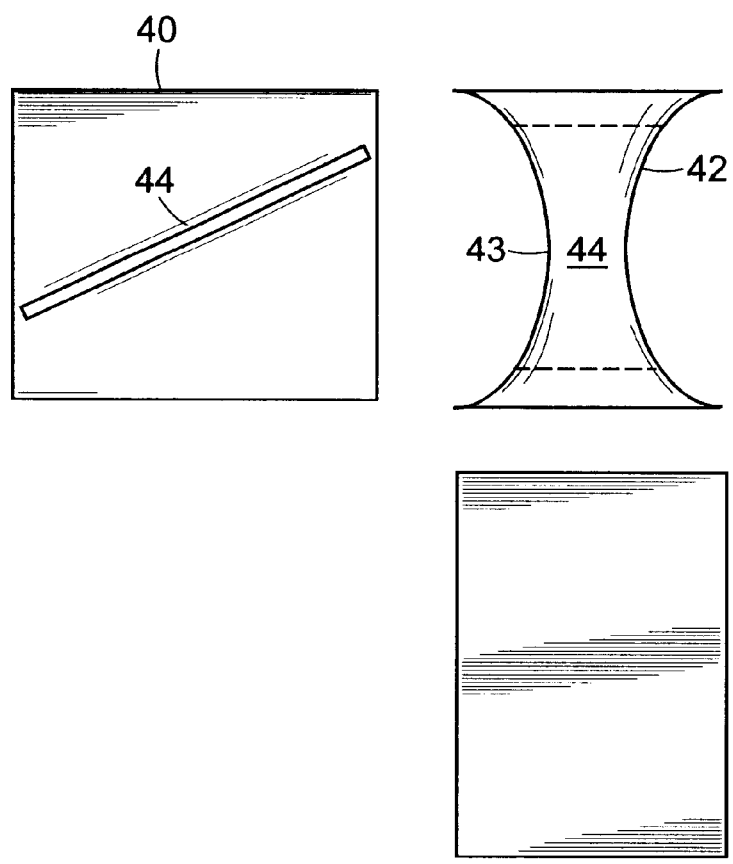
FIG. 5 illustrates one embodiment of a saw guide for use with the present invention.
Figure 6A:
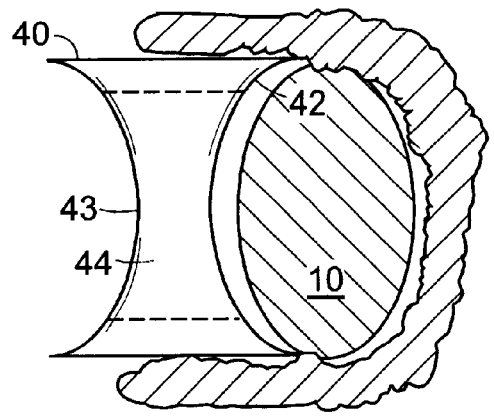
FIG. 6A is a top view of the saw guide of FIG. 5 positioned against the femur in the manner shown in FIGS. 4A–D.
Figure 6B:
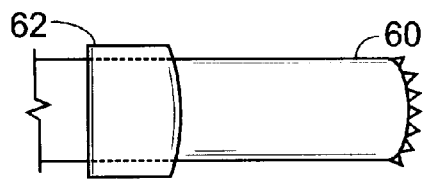
FIG. 6B shows a saw blade with a stop for use with the present invention.
Figure 6C:
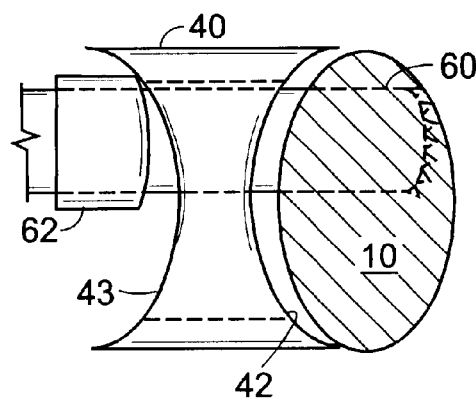
FIG. 6C shows the saw blade of FIG. 6B in use with the saw guide of FIG. 6A.

Subsequent to the formation of the tunnel 36, a saw guide 40 may be positioned against a lateral surface of the femur 10 and attached to the support structure 30 (FIGS. 4A–4D). The attachment of the saw guide 40 to the support structure 30 may be accomplished using a clamping mechanism 45 or other means known in the art. Once secured, the saw guide 40 permits a fast and accurate cut to be made across the width of the femur 10. The saw guide 40, shown in FIG. 5, includes opposing concave surfaces 42 and 43. The concave surfaces are designed so that surface 42 may engage the femur 10 (FIGS. 6A and 6C), while surface 43 may guide a cutting blade along a path defined by its concave surface. A slot 44 extends from concave surface 43 to concave surface 42 and is positioned diagonally across the guide 40. As illustrated in FIG. 4B, when the saw guide 40 is situated against the lateral surface of the femur 10 adjacent the angular deformity, the slot 44 extends from a proximal portion 46 of the femur to a distal portion 48 and lies diagonally from the anterior surface A to posterior surface P of the femur 10. In this manner, a predictable, and relatively ellipsoidal arc, similar to surface 43, can be produced on the medial surface of the femur 10 when a cut is made obliquely along the lateral surface. The saw guide 40 is intended for use with a horizontally situated oscillating blade 60 (FIG. 6B). Blade 60 is preferably designed with a rounded portion. The rounded portion on blade 60 allows the femur 10 to be cut, as shown in FIG. 6C, without the need to strip the periosteum (i.e., soft tissue) from all sides of the femur 10 (FIG. 6A). The blade 60 is also provided with a stop 62, which conforms to concave surface 43 of the saw guide 40, to accurately control the distance the blade 60 extends once it has penetrated through the femur 10. The ability to control the extension distance prevents tissue on the other side of the femur from being damaged by the blade 60. The stop 62, when used in combination with the blade 60, allows for controllable extension of the blade 60 to a distance of a millimeter or less from the opposite side of the femur 10. In one embodiment, the blade 60 is detachable and adjustable, for example, by means of a set screw, so that the depth of the cut may be further controlled and precisely varied. The ability to precisely control the cutting depth obviates the possibility of injury to medial structures, even though the periosteum (i.e., soft tissue) is not stripped. If desirable, prior to cutting the femur 10, a depth gauge may be used as a tap so that holes may subsequently be drilled through the femur 10 sequentially from the proximal anterior position to the distal posterior position along the slot 44 of the saw guide 40. This procedure will allow for a very precise measurement of the ellipsoidal arc.

Figure 7A:
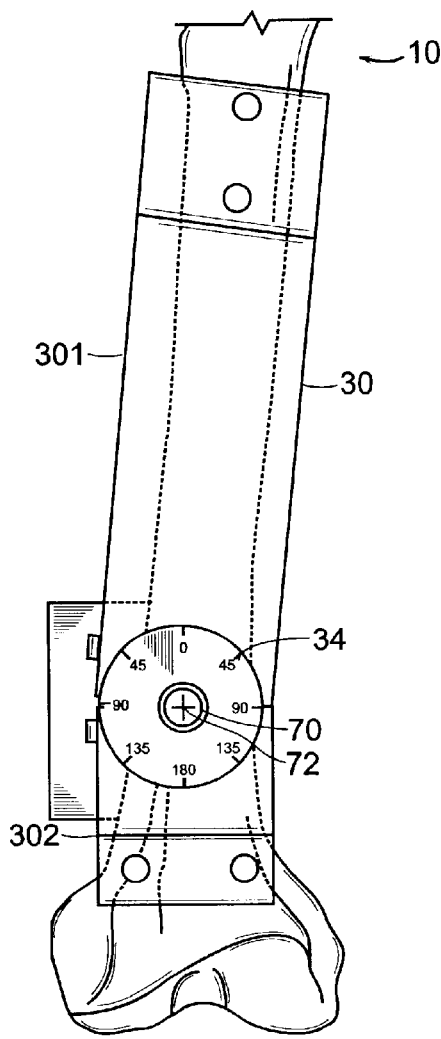
FIGS. 7A–B illustrate a femur having a bone anchor extending across a cut made by the saw and guide of FIGS. 5 and 6A–C.
Figure 7B:
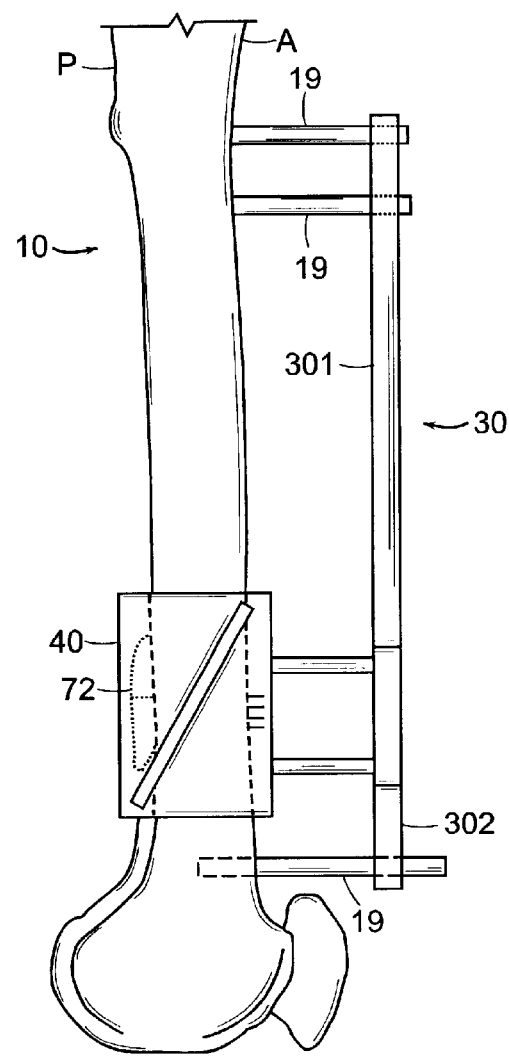

Referring now to FIGS. 7A and 7B, after the tunnel 36 has been formed, an oblique cut may be made through the slot 44 of the saw guide 40, shown in FIG. 7B. The oblique cut is preferably made on a surface of the femur 10 which is parallel to the tunnel 36. In the present illustration, the cut is made on the lateral surface of the femur 10. The oblique cut is initially formed partially across the femur 10, from the posterior surface P toward the anterior surface A. In a preferred embodiment, the cut extends from approximately ⅔ to approximately ¾ of the way across the width of the femur 10.

Figure 8C:
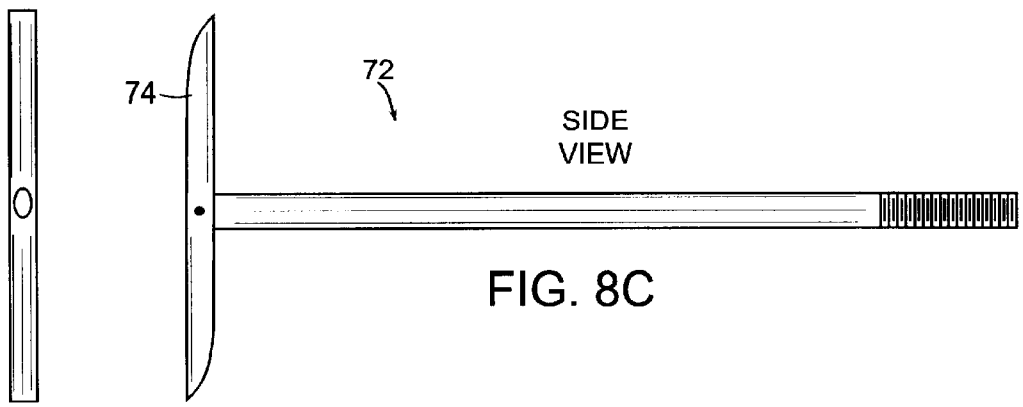
Figure 8D:

Once the initial partial cut has been made, a bone anchor assembly for maintaining the bone pieces in approximation may be placed through the tunnel 36 and loosely secured therein. In one embodiment of the present invention, when a tunnel similar to cylindrical tunnel 36 (FIGS. 3B and 3D) is formed in the femur 10, a bone anchor assembly 72, as shown in FIGS. 8A and 8B, is employed. The bone anchor 72 includes an elongated body 73 for placement through the cylindrical tunnel 36. The bone anchor 72 further includes a pivoting member 74 situated, at a first end 75 of the body 73 and a threaded portion 76 located at the second end 77 of the body 73. In its non-deployed position in FIGS. 8A and 8B, the pivoting member 74 extends from the first end 75 and is axially aligned to the body 73. The pivoting member 74, after being introduced through opening 70 in goniometer 34 and into the tunnel 36, is capable of being deployed into a position transverse to the body 73 (FIGS. 8C–E) to act as an anchor against the posterior surface P of the femur 10. Once the bone anchor 72 is deployed, the threaded member 76 on the body 73 preferably remains extended from the anterior surface A of the femur 10. In this manner, a complementarity threaded member 78, for example, a washer, may engage the threaded portion 76 to form a locking mechanism to secure the bone anchor against the bone pieces. Of course other locking mechanisms may be provided so long as they remain capable of securing the bone anchor within the tunnel while maintaining the bone pieces in close approximation. Prior to placing the bone anchor 72 through the tunnel, a rigid sleeve 79 may be provided extending along the length of the tunnel 36. The sleeve 79, in one embodiment, includes a substantially smooth interior surface, so that it may act as a lining along which the bone anchor 72 can easily slide through the tunnel 36 without interference from loose tissue which may be present in the tunnel. In addition, the sleeve 79 assures a close and precise fit within the tunnel 36 so that translation of the bone pieces, often associated with other osteotomy procedures, may be avoided. The sleeve 79 may also be used to provide rigidity to the tunnel and a limit to the compression experienced by the bone when the anchor assembly is securely tightened in place.

Figure 8E:
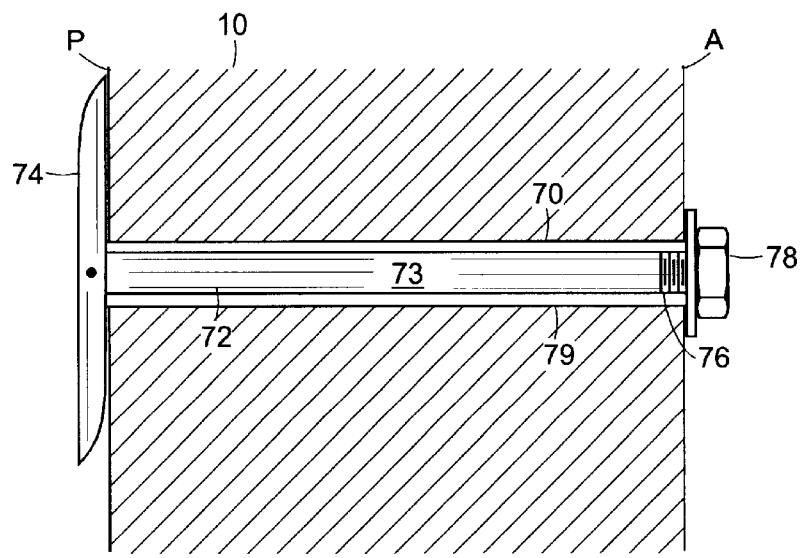
FIG. 8E is a bone anchor shown in FIGS. 8A–D extending through a femur.
Figure 15A:
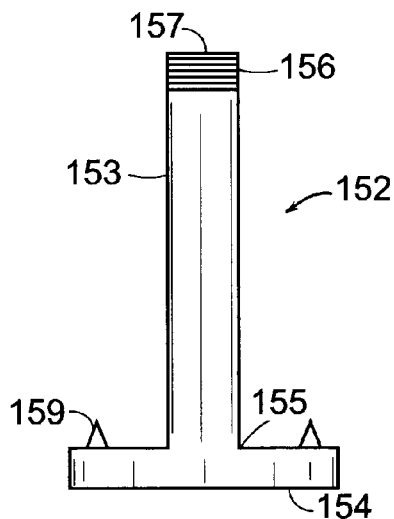
FIG. 15A shows a bone anchor in accordance with another embodiment of the present invention.
Figure 15B:
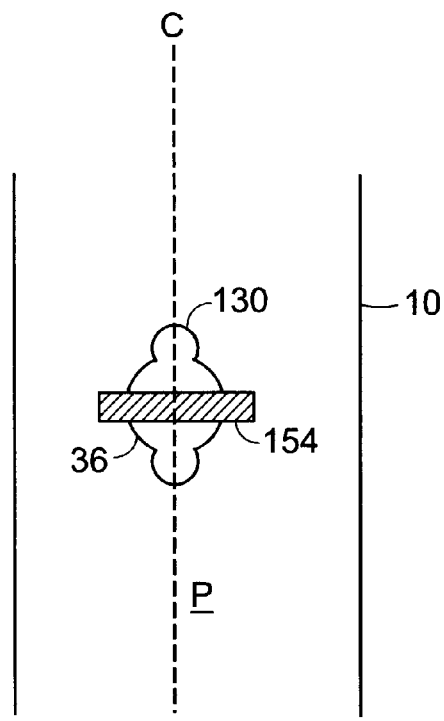
FIG. 15B is a end view of the tunnel formed in FIG. 13A having the device in FIG. extending therethrough.

In another embodiment of the invention, looking now at FIGS 15A–B, when a tunnel is formed with opposing passageways 130, a bone anchor 152 is employed. The bone anchor 152, in a preferred-embodiment, includes an elongated body 153 for placement through the tunnel 36. The bone anchor 152 further includes a cross member 154 situated at a first end 155 of the body 153, and a threaded portion 156 at a second end 157 of the body 153. This design is similar to that of FIGS. 8A and 8B, except that the cross member 154 is configured in fixed relation to the body 153, whereas in FIGS. 8A–B, the corresponding member 74 is pivoted. The cross member 154 is transverse to the body 153 so as to act as an anchor against the posterior surface P of the femur 10. This embodiment of a bone anchor is used in connection with the tunnel configuration discussed above in connection with FIGS. 13A–C and 14A–D, and is inserted as illustrated in FIG. 15B. Prior to placing the bone anchor through the tunnel 36, shown in FIG. 15B, a rigid sleeve (not shown) having a cross-sectional profile similar to that of tunnel 36 is placed within the tunnel. This rigid sleeve, similar to rigid sleeve 79, acts as a lining along which the bone anchor 152 can easily slide through the tunnel 36 without interference from loose tissue within the tunnel. The sleeve may also act to provide rigidity to the tunnel and to limit the compression experienced by the bone when the bone anchor 152 is securely tightened in place. To place the bone anchor 152 through the tunnel 36, the distal end 155 of the bone anchor is initially positioned so that the cross member 154 spans from one passageway 130 to the opposing passageway 130. Thereafter, the cross member 154 may be pushed through the tunnel, along the rigid sleeve, toward the posterior surface P of the femur 10, as shown in FIG. 8E and 15B. Once the cross member 154 extends from the tunnel 36 and passageways 130, the bone anchor 152 may be rotated in either a clockwise or counterclockwise direction so that the cross member 154 becomes offset from the opposing passageways 130. In one embodiment, the cross member 154 may be positioned at approximately ninety degrees to the passageways 130, as illustrated in FIG. 15B. The cross member 154 is then pulled against the posterior surface P of the femur 10. To secure the cross member 154 in place, the threaded portion 156 of the bone anchor 152 preferably remains extended from the anterior surface of the femur 10 so that a mating internally threaded member 158 may engage the threaded portion 156 to form a locking mechanism through the tunnel 36 to secure the bone anchor 152 against the bone pieces. Spikes or protrusions 159 may be provided on cross member 154 so as to dig into the posterior surface P of the femur 10. In this manner, the cross member 154 may securely act as an anchor against the posterior surface P of the femur 10.

Figure 16A:
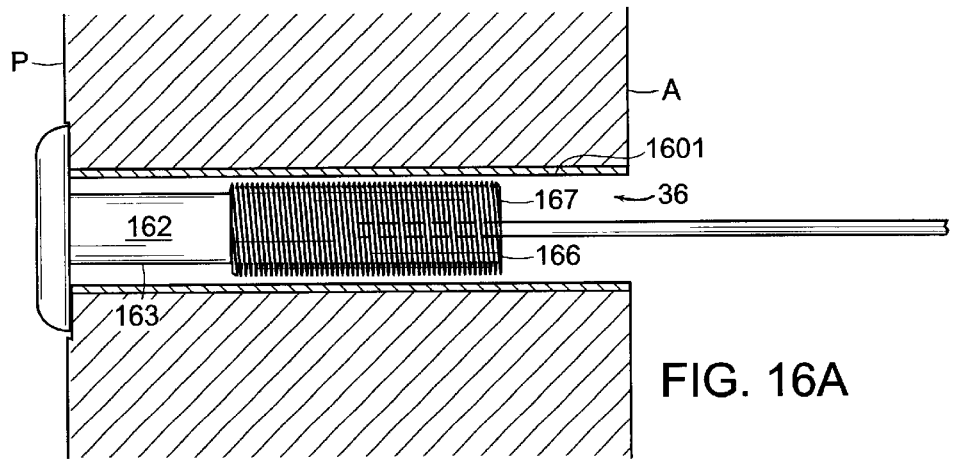
FIGS. 16A–C show a bone anchor in accordance with a further embodiment of the present invention.
Figure 16B:
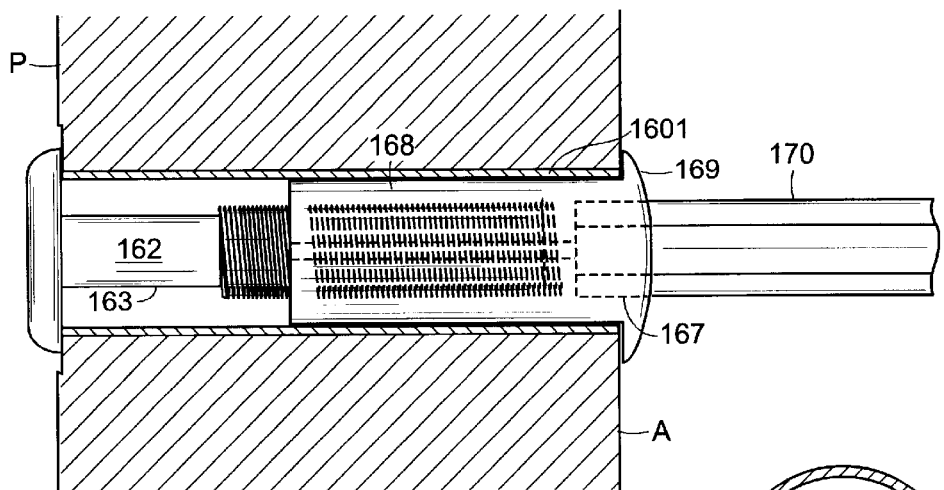
Figure 16C:
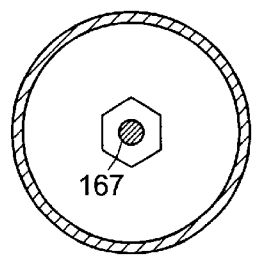

In a further embodiment of the invention, looking now at FIGS. 16A–B, bone anchor 162 is modified from that shown in FIG. 15, so that its elongated body 163 does not extend beyond the tunnel 36. To secure such a modified bone anchor within tunnel 36, bone anchor 162, in an embodiment, is designed so that the elongated body 163 is threaded to receive a complementary threaded member 168. Threaded member 168, as shown in FIG. 16B, is capable of extending into the tunnel 36 and over the body 163. The threaded member 168, as shown in FIG. 16B, is preferably provided with a flared end 169 to engage the anterior surface A of the femur 10. In addition, the threaded member 168 preferably includes a diameter which approaches that of the tunnel 36. In this manner, the threaded member 168 allows the bone anchor 162 to securely engage against the bone pieces. The threaded member 168 also preferably includes a recess 167 for receiving a driver 170, such as an alien wrench, designed to rotate the threaded member 168 onto the elongated body 163. Recess 167 may be of any shape for sufficiently receiving a complementary-shaped driver 170. In a preferred embodiment of the invention, recess 167, as shown in FIG. 16C, and driver 170 are hexagonal in shape. A sleeve 1601 may also be provided extending along the entire length of the tunnel to provide rigidity to the tunnel 36.

Figure 17:
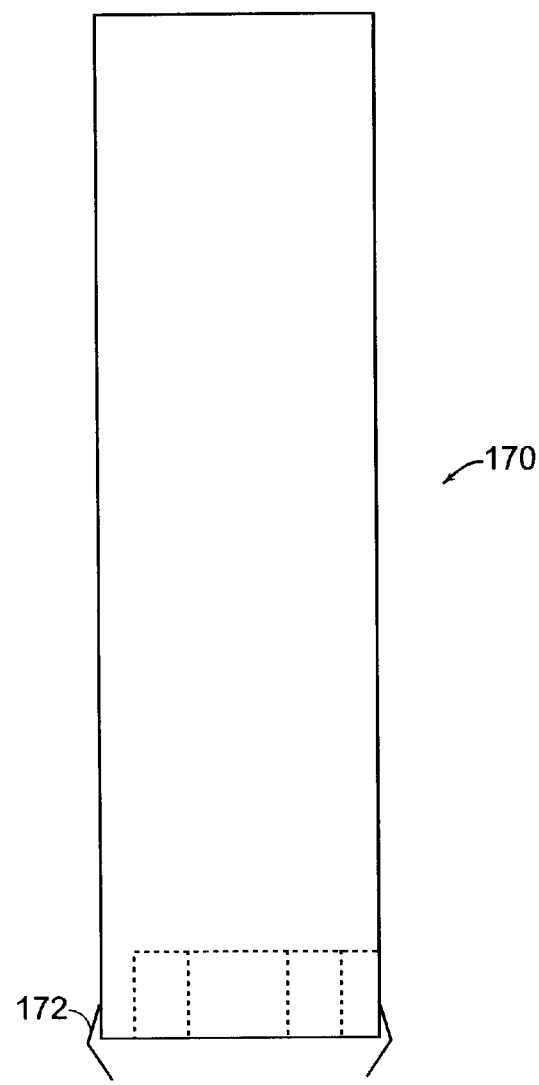
FIG. 17 shows a driver for use with the device shown in FIGS. 16A–C.

Referring now to FIG. 17, driver 170 includes retractable teeth 172 at its distal end for engaging recess 167 of member 168. The teeth allow the member 168 to be maintained on the driver 170 when the member is being maneuvered into the tunnel 36 and rotated onto the elongated body 163. Once the member 168 is securely tightened about elongated body 163, the teeth 172 may be retracted, for example, by a switch (not shown) on the driver, and the driver 170 removed from the tunnel 36.

The bone anchor, in the illustrated embodiments, may be cannulated to receive a guidewire so as to facilitate the placement of the bone anchor through the tunnel 36. The driver for placing the threaded member onto the elongated body of each bone anchor may also be cannulated. In addition, because the bone anchor must come in contact with biological tissue and must be sufficiently strong, so as to maintain the bone pieces in approximation, it is preferable that the bone anchor be made from a biocompatible material, for instance, stainless steel or plastic. The bone anchor may also made from a bioabsorbable material, for instance polylactic acid (PLA).

The angle of the correction on the femur 10 may next be determined. Looking now at FIGS. 12A–D, in accordance with one embodiment of the present invention, intra-articular pressure between the femur 10 and the tibia may next be measured by using a pressure transducer 120. In general, intra-articular pressure between the femur and the tibia tends to vary from individual to individual and is often dependent on the height, weight and age of the individual. To this end, the employment of a pressure transducer allows for variations in individual characteristics to be taken into account, so that, for each particular individual, a more precise cut angle can be made on the femur 10. Otherwise, the cut may be inappropriate, and may result in a bone alignment that is insufficient to reduce the intra-articular pressure between the femur and the tibia. According to an embodiment of the invention, the angle of the cut determined from intra-articular pressure measurements preferably allows pressure applied by the femur on its lateral femoral condyle and medial femoral condyle to substantially approach a desired ratio within a physiologic tolerance, once the correction has been made.

The pressure transducer 120, in a preferred embodiment of the invention, is a TekScan pressure transducer, manufactured by TekScan Inc. of Boston, Mass. Pressure transducer 120 includes a sensing tip 1201 and a body 1202 along which measurement information may be transmitted to a reading display (not shown). Looking now at FIGS. 12C and 12D, to measure the contact pressure within the intra-articular space of, for example, a right knee 122 of an individual, in one embodiment of the invention, a cannula 123 is first introduced through a lateral portal 124, such that its proximal end 1230 remains on the exterior of the knee 122. The cannula 123 is preferably hollow to receive a trocar 125. Once the cannula 123 is in place, the pressure transducer 120 may be introduced into the knee 122 by first maneuvering its sensing tip 1201 through the proximal end 1230 of the cannula 123, then pushing the body 1202 medially along the cannula using the trocar 125. A grasper 126 is next introduced through a medial portal 127 to pull the pressure transducer 126 from the cannula 123 into the knee. The sensing tip 1201 of pressure transducer 120, looking again at FIG. 12A, may subsequently be positioned about the lateral aspect of the knee, for example, under the lateral femoral condyle 128. Once in position, the lateral condyle 128 is made to press down onto the sensing tip 1201, in order to measure the contact pressure thereat. The sensing tip 1201 is then maneuvered to the medial aspect of the knee, for example, under the medial femoral condyle 129, and the contact pressure again measured. By measuring the contact pressure along at least two points within the intra-articular space, for example, the lateral and medial condyles, a cut may subsequently be made across the femur 10, such that after realignment of the bone pieces, the intra-articular pressure about the lateral and medial aspects of the knee joint substantially approaches a desirable ratio within a physiologic tolerance.

Although the present invention contemplates the use of the pressure transducer in order to determine the angle of correction, it should be appreciated that other methods may also be employed. Examples include but are not limited to, radiographic means, visual means, MRI, laser, and bone scans. These and other similar visualization methods are adequate, so long as they permit the actual amount of correction in the deformed bone to approach a physiologic tolerance.

Figure 9A:
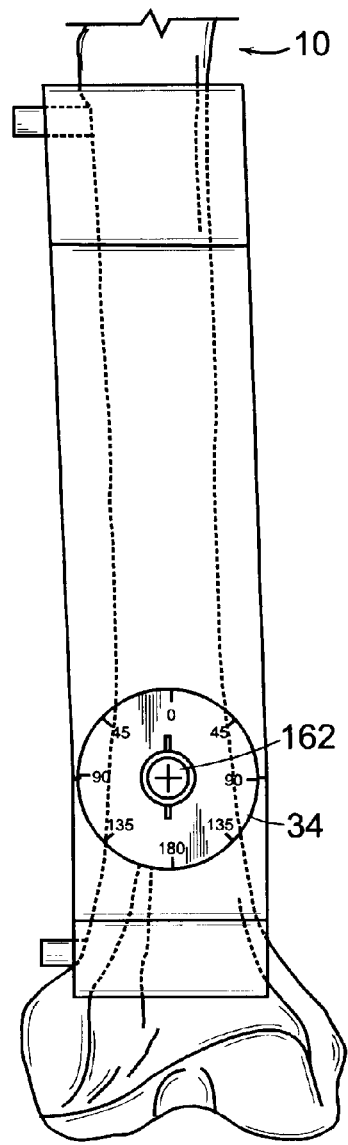
FIGS. 9A–B illustrate a femur having been corrected of its angular deformity.
Figure 9B:
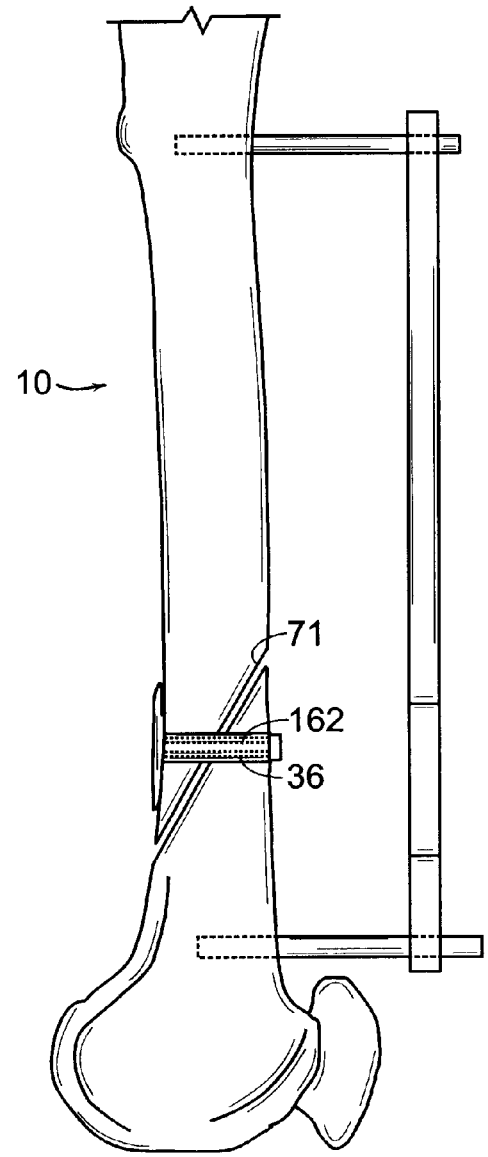
Figure 10A:
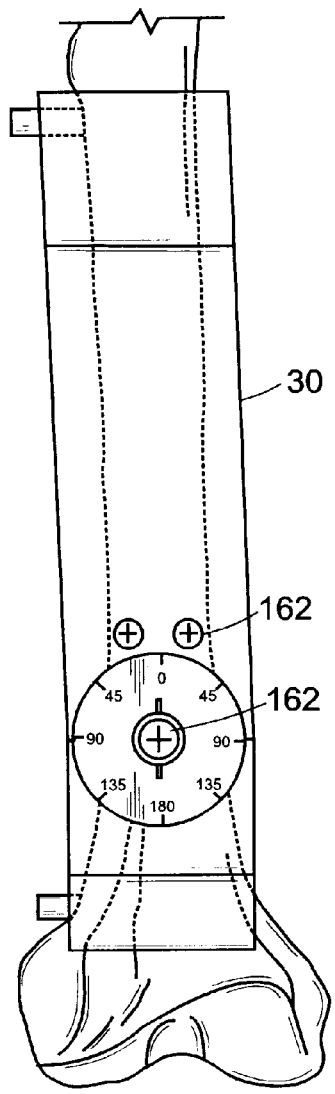
FIGS. 10A–B show the femur of FIGS. 9A–B with additional bone anchors.
Figure 10B:
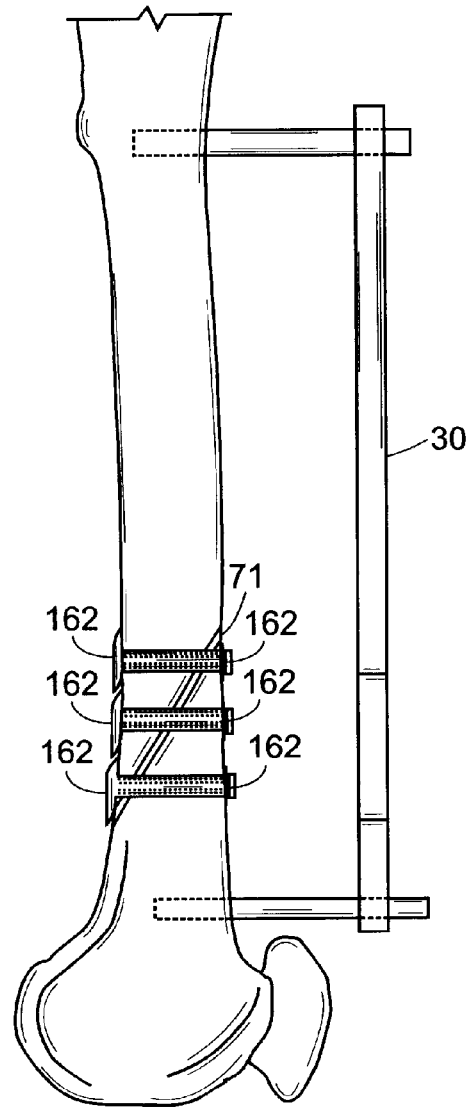

Once the contact pressure has been determined, saw blade 60 may be inserted into the slot 44 of guide 40, and into the partial oblique cut on the femur 10 at a position distal to the loosely secured bone anchor, for instance, bone anchor 162. The partial oblique cut is then completed across the femur 10 to form two bone pieces. It should be appreciated that each of the resulting bone pieces includes a portion of the tunnel 36, and is held in position relative one another by the bone anchor and the support structure 30. Looking now at FIG. 9A, the bone pieces may be pivoted relative to one another about the bone anchor 162 by the precisely geared goniometer 34 until a desired angle of alignment is reached, for instance, an angle which conforms to the amount of correction previously determined. In this manner, a precise degree of correction and alignment between the bone pieces may subsequently be achieved. Once the correction and alignment have been obtained, the bone anchor 162 is tightly secured against the femur 10 at cut 71 (FIG. 9B), so that the bone pieces may be pulled against one another. The bone anchor 162, when secured through the tunnel 36, acts to pull the bone pieces in a direction transverse to the cut 71 so that the bone pieces may remain in approximation and alignment. Although reference has been made to the bone anchor 162, it should be understood that bone anchors 152 or 72 may also be used.

Figure 18:
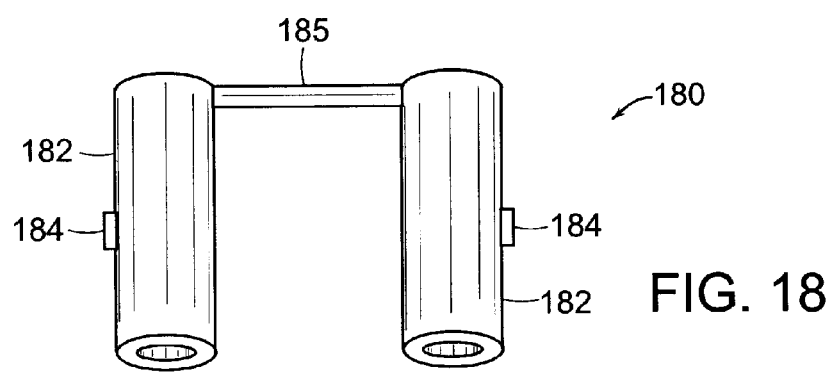
FIG. 18 illustrates a guide for forming multiple bone anchor tunnels in accordance with an embodiment of the present invention.

To ensure that alignment between two bone pieces is maintained and no subsequent translational movement will occur, multiple bone anchors 162 may be secured through the femur 10 along the cut 71 (FIGS. 10A–B and 11A–B). To form the tunnels that will accommodate the additional bone anchors, referring now to FIG. 18, an apparatus 180 is employed. Apparatus 180, in one embodiment of the invention, includes a pair of parallel substantially cylindrical members 182, configured so that either may be positioned within the opening 70 of goniometer 34. The members are coupled to one another by a connector 185. Each member 182 may include a protrusion 184, similar to protrusion 1465 illustrated in FIG. 14B, for engaging slot 75 in goniometer 34 to prevent the apparatus 180 from rotating during formation of the tunnel 36 and/or passageways 130. When one cylindrical member 182 is placed within the opening 70, the other cylindrical member 182 is preferably extended by connector 185 beyond the goniometer 34 for subsequently guiding a coring reamer into the femur 10. The connector 185 may be adjustable in order to vary the distance between members 182 and thus between the tunnels formed. Each cylindrical member 182 is provided with an inner diameter designed to accommodate either cylindrical guide 145 or guide 146, discussed above in connection with FIGS. 14A–B. In an embodiment, the member 182 that is not to be positioned within the opening 70 of the goniometer 34 may be substituted with a ring. The ring is preferably sufficiently rigid and includes an inner diameter that is capable of accommodating the either guide 145 or guide 146. The procedure previously described may thereafter be employed, that is drilling a tunnel through the femur, placing a bone anchor through the tunnel, and securely tighten the bone anchor against the femur.

Figure 11A:
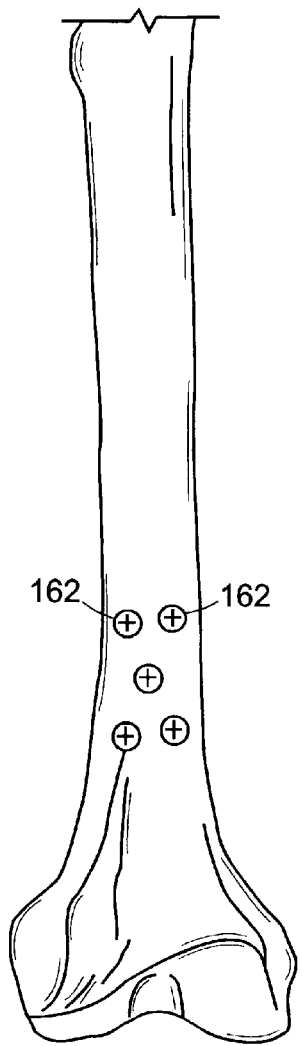
FIGS. 11A–B illustrate the end results of a corrected femur of FIGS. 10A–B.
Figure 11B:
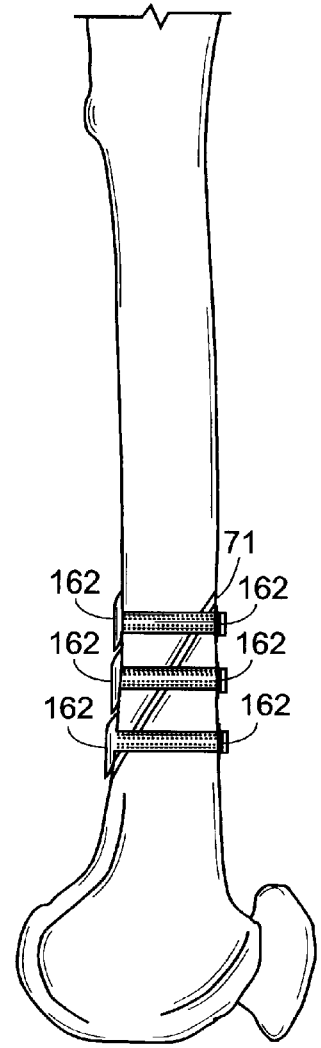
Figure 12B:
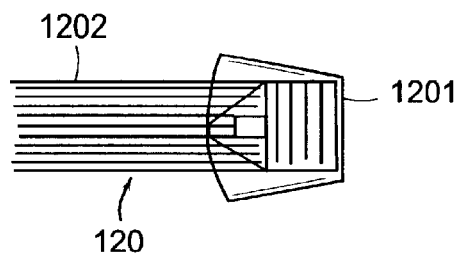
FIG. 12B shows the pressure transducer shown in FIG. 12A.
Figure 12A:
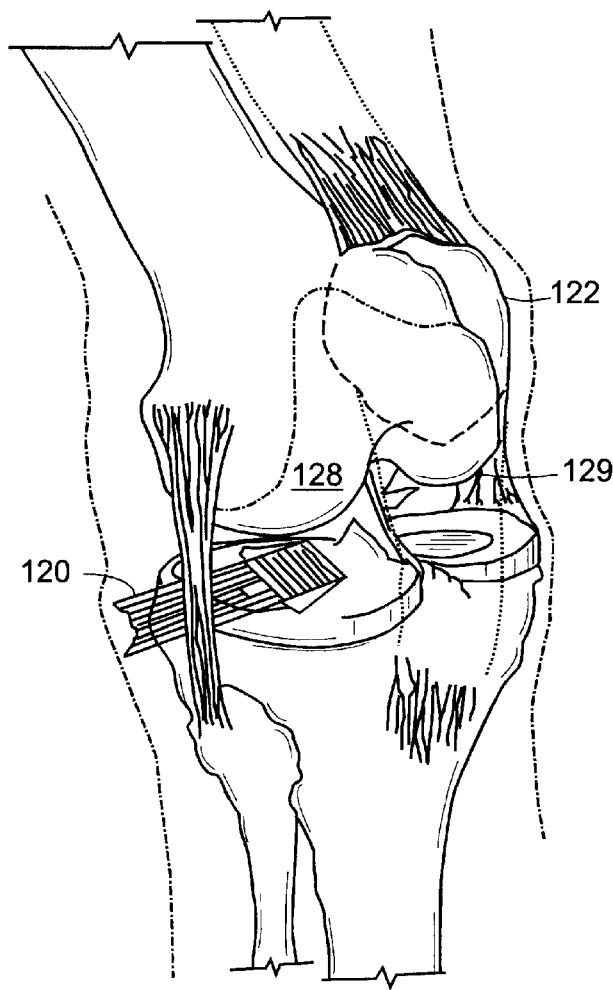
FIG. 12A illustrates a knee with a pressure transducer portion therein.
Figure 12C:
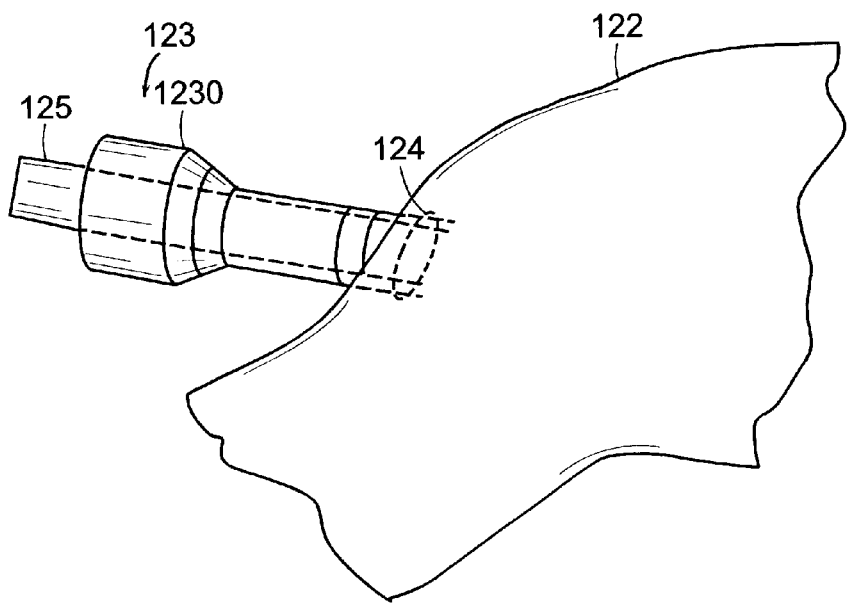
FIGS. 12C–D illustrate a knee having a cannula and trocar inserted through a lateral portal and a grasper inserted through a medial portal.
Figure 12D:
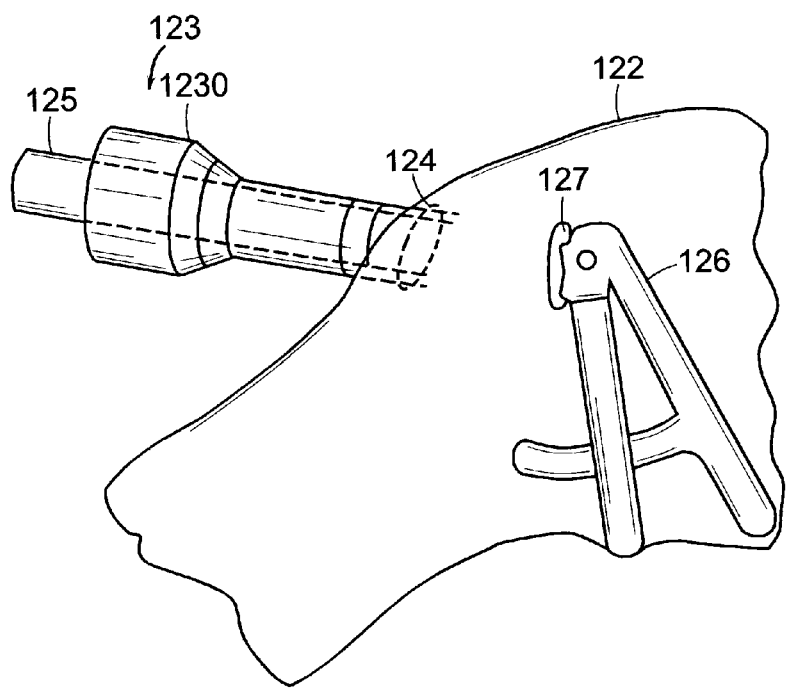

When securing with additional bone anchors 162, the support structure 30 and/or the goniometer 34 may be provided with a locking mechanism (not shown) so that the alignment between the bone pieces may be maintained prior to the placement of the additional bone anchors 162 into the femur 10. In one embodiment of the invention, at least two bone anchors 162 are used. The location and number of the additional bone anchors 162, to a certain extent, are limited only by the size of the bone. FIG. 11A illustrates a configuration wherein a total of five bone anchors 162 are positioned in the femur 10. The use of multiple bone anchors provides added rigidity to the cut and resistance to translational movement between the bone pieces, such that the support structure 30 may subsequently be removed. In addition, as the fixation is sufficiently secured, no external fixators, for instance, transfixion screws, lag screws, and similar devices will be needed.

Although the above described methods are directed to femoral osteotomy, the same methods are applicable to tibial osteotomy. It is contemplated that the sequence of steps outlined above would be followed. However, unlike the femoral osteotomy, the tibial osteotomy is distal to the tibial tubercle and extends from a proximal posterior position on the tibia to a distal anterior position.

Figure 19A:
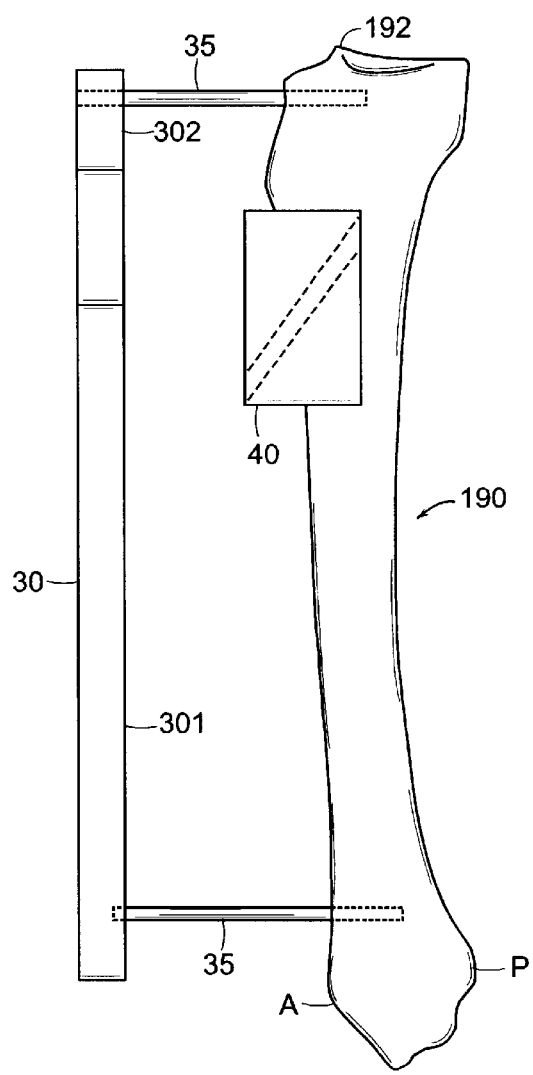
FIGS. 19A–D illustrate a tibial osteotomy in accordance with an embodiment of the present invention.
Figure 19B:
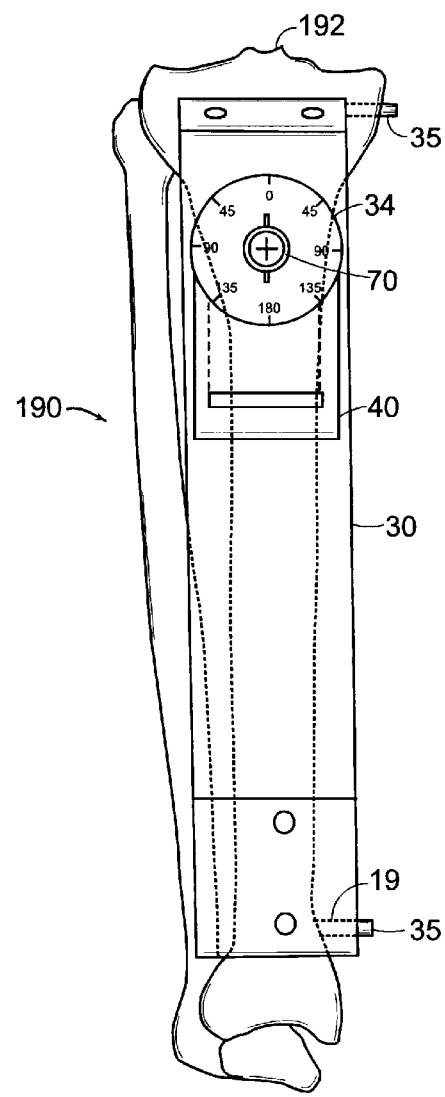
Figures 19C, 19D:
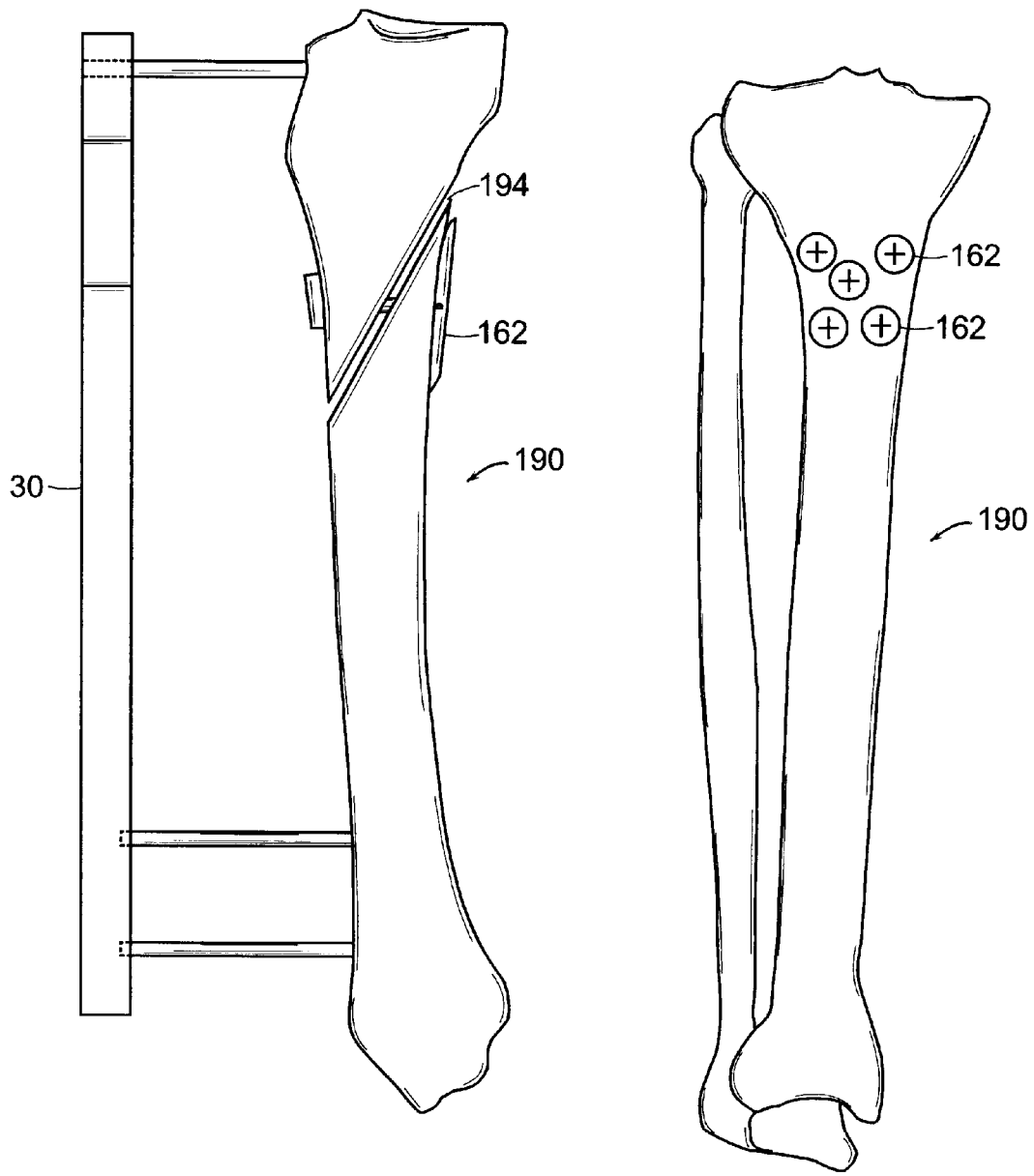

In order to achieve such a cut, referring now to FIGS. 19A–D, the support structure is positioned along the anterior surface of the tibia 190 such that the first portion 301 is distal to the tibia tubercle 192 and the second portion 302 is proximal to the tibial tubercle 192. The support structure 30 of FIGS. 19A–D corresponds to the embodiment shown in FIG. 3C, and is affixed to subcutaneously insertable pins 19 on the medial surface of the tibia 190 byway of bars 35. In an alternate embodiment, the support structure 30 may correspond to the embodiment shown in FIG. 3A, and may be affixed to multiple subcutaneously insertable pins 19 on the anterior surface of the tibia 190, as shown in FIG. 19B. Furthermore, whereas in a femoral osteotomy the guide 40 is placed on a lateral surface of the femur 10, in tibial osteotomy the guide 40 is placed of the anterior surface of the tibia 190. The position of the guide 40, however, is distal to the opening 70 in goniometer 34 and provides a cut that traces the geometry of the posterior surface of the tibia. More particularly, as seen from the medial surface of the tibia 190, the cut is similar to cut 194 in FIG. 19C. Once the cut is made, the procedure described above in connection with the femoral osteotomy may be employed to secure a bone anchor 162 across the cut 194. Multiple anchoring pins 162 (FIG. 19D) may also be employed to ensure a secure alignment of the tibial bone pieces. In general, a tibial osteotomy may be easier to perform than a femoral osteotomy in terms of fixation, but slightly more difficult in terms of cutting.

While the invention has been described in connection with specific embodiments thereof, it will be understood that it is capable of further modification. This application is intended to cover any variations, uses, or adaptations of the invention and including such departures from the present disclosures as come within known or customary practice in the art to which the invention pertains. For example, the above procedure may also be used to easily fix a horizontal, spiral oblique fracture of the humerus, as well as fractures in other bones of the body.

What is claimed is:

1. A device for maintaining in approximation bone pieces produced from an osteotomy procedure, the device comprising:

an elongated body for extending into a tunnel between the bone pieces, the body having a distal and a proximal end;

an anchoring member rotatably positioned at the end transverse to the body to engage one bone piece;

a locking mechanism at the proximal end of the body to engage the other bone piece, such that the bone pieces may be pulled against one another between the rigid member and the locking mechanism wherein the locking mechanism comprises a threaded portion along the proximal end of the body and a complementarity threaded member for engaging the threaded portion; and a rigid sleeve having a substantially smooth interior surface extending along the length of the bone tunnel so as to permit the elongated body to slide through the tunnel.

2. A device as set forth in claim 1, wherein the elongated body has a length sufficiently long so as to allow the device to extend through both bone pieces.

3. A device as set forth in claim 2, wherein the locking mechanism remains substantially outside of the bone tunnel.

4. A device as set forth in claim 1, wherein the elongated body is situated entirely within the bone tunnel.

5. A device as set forth in claim 4, wherein the locking mechanism extends into the bone tunnel.

6. A device as set forth in claim 1, wherein the rotatably positioned anchoring member is axially aligned to the elongated body when said anchoring member is in a non-deployed mode.

7. A device as set forth in claim 1, wherein the rotatably positioned anchoring member is capable of being deployed after introduction into the bone tunnel, such that said anchoring member is transverse to the elongated body when in a deployed mode.

8. A device for maintaining in approximation bone pieces produced from an osteotomy procedure, the device comprising:

an elongated body for extending into a tunnel between the bone pieces, the body having a distal end and a proximal end;

an anchoring member positioned at the distal end of the body for engaging against one bone piece; and a locking mechanism at the proximal end of the body to engage the other bone piece, such that the bone pieces may be pulled against one another between the anchoring member and the locking mechanism;

a locking mechanism at the proximal end of the body to engage the other bone piece, such that the bone pieces may be pulled against one another between the rigid member and the locking mechanism wherein the locking mechanism comprises a threaded portion along the proximal end of the elongated body and a complementarily threaded member for engaging the threaded portion; and a rigid sleeve having a substantially smooth interior surface extending along the length of the bone tunnel so as to permit the elongated body to slide through the tunnel.

9. A device as set forth in claim 8, wherein the device is made from a biocompatible material sufficiently strong to pull the bone pieces against one another.

10. A device as set forth in claim 8, wherein the anchoring member is pivotally-connected to the elongated body.

11. A device as set forth in claim 8, wherein the elongated body has a length sufficiently long so as to allow the device to extend through both bone pieces.

12. A device as set forth in claim 11, wherein the locking mechanism remains substantially outside of the bone tunnel.

13. A device as set forth in claim 8, wherein the elongated body is situated entirely within the bone tunnel.

* * * * *